(12) United States Patent
Rondoni et al.

(10) Patent No.: US 12,343,545 B2
(45) Date of Patent: Jul. 1, 2025

(54) SYSTEM AND METHOD OF MONITORING FOR AND REPORTING ON PATIENT-MADE STIMULATION THERAPY PROGRAMMING CHANGES

(71) Applicant: INSPIRE MEDICAL SYSTEMS, INC., Golden Valley, MN (US)

(72) Inventors: John Rondoni, Plymouth, MN (US); Quan Ni, Golden Valley, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 1267 days.

(21) Appl. No.: 17/096,433

(22) Filed: Nov. 12, 2020

(65) Prior Publication Data

US 2021/0106836 A1    Apr. 15, 2021

Related U.S. Application Data

(63) Continuation of application No. 15/836,224, filed on Dec. 8, 2017, now Pat. No. 10,850,109, which is a
(Continued)

(51) Int. Cl.
*A61N 1/372* (2006.01)

(52) U.S. Cl.
CPC ..... *A61N 1/37264* (2013.01); *A61N 1/37217* (2013.01); *A61N 1/37247* (2013.01)

(58) Field of Classification Search
CPC ............ A61N 1/37264; A61N 1/37217; A61N 1/37247
See application file for complete search history.

(56) References Cited

U.S. PATENT DOCUMENTS

| 6,675,048 B2 | 1/2004 | McGraw et al. |
| 7,505,815 B2 | 3/2009 | Lee et al. |

(Continued)

FOREIGN PATENT DOCUMENTS

| JP | 2004537355 A | 12/2004 |
| JP | 2012-506759 A | 3/2012 |

(Continued)

OTHER PUBLICATIONS

Boston Scientific, "Precision Spectra Spinal Cord Stimulation System", 2013, 15 pages.
(Continued)

*Primary Examiner* — Lindsey G Wehrheim
(74) *Attorney, Agent, or Firm* — DICKE, BILLIG & CZAJA, PLLC

(57) ABSTRACT

A programmer is configured to effect communication with, and programming of, an implantable medical device configured to deliver neurostimulation therapy. The programmer comprises a display, such as touch screen display, and a processor comprising memory and coupled to the display. An interface is coupled to the processor and configured to receive therapy settings data indicative of current therapy settings operative in the implantable medical device and any modifications made to the therapy settings by a patient. The processor is configured to determine if one or more therapy settings have been modified since the last interaction with the patient, and coordinate displaying of the current therapy settings, the one or more therapy settings modified by the patient, and a previous state of the one or more therapy settings modified by the patient on the display.

21 Claims, 19 Drawing Sheets

Related U.S. Application Data continuation of application No. 14/689,469, filed on Apr. 17, 2015, now Pat. No. 9,839,786.

(56) References Cited

U.S. PATENT DOCUMENTS

| | | |
|---|---|---|
| 8,249,716 B2 | 8/2012 | Tano et al. |
| 8,843,203 B2 | 9/2014 | Lee et al. |
| 9,393,420 B2 | 7/2016 | Almendinger et al. |
| 9,744,360 B2 | 8/2017 | Kishawi et al. |
| 2002/0016616 A1 | 2/2002 | McGraw et al. |
| 2005/0085865 A1 | 4/2005 | Tehrani |
| 2006/0052844 A1* | 3/2006 | Newman ............ A61N 1/36021 607/67 |
| 2006/0190047 A1 | 8/2006 | Gerber et al. |
| 2008/0221644 A1 | 9/2008 | Vallapureddy et al. |
| 2009/0287103 A1 | 11/2009 | Pillai |
| 2010/0137938 A1 | 6/2010 | Kishawi et al. |
| 2013/0268026 A1 | 10/2013 | Rao et al. |
| 2014/0067005 A1 | 3/2014 | Kaula et al. |
| 2014/0277248 A1 | 9/2014 | Younker et al. |

FOREIGN PATENT DOCUMENTS

| | | |
|---|---|---|
| WO | 03008038 A1 | 1/2003 |
| WO | 2008084711 A | 7/2008 |
| WO | 2010062622 A2 | 6/2010 |
| WO | 2013134763 A2 | 9/2013 |

OTHER PUBLICATIONS

International Search Report and Written Opinion dated Jun. 27, 2016 from PCT Application No. PCT/US2016/026954, 12 pages.
Boston Scientific, Bionic Navigator Software Guide, 2009, 156 pages.

* cited by examiner

| Param | Time at Each Level (%) | Trend/ Histogram | AHI at Each Level | ODI at Each Level | Flag |
|---|---|---|---|---|---|
| A | %@ L1-Ln | | @ L1-Ln | @ L1-Ln | ○ |
| B | %@ L1-Ln | | @ L1-Ln | @ L1-Ln | ○ |
| C | %@ L1-Ln | | @ L1-Ln | @ L1-Ln | ● |

Figure 12
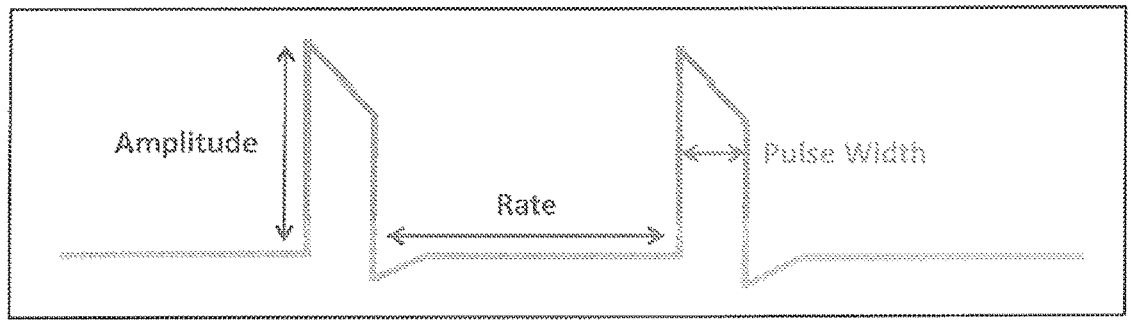
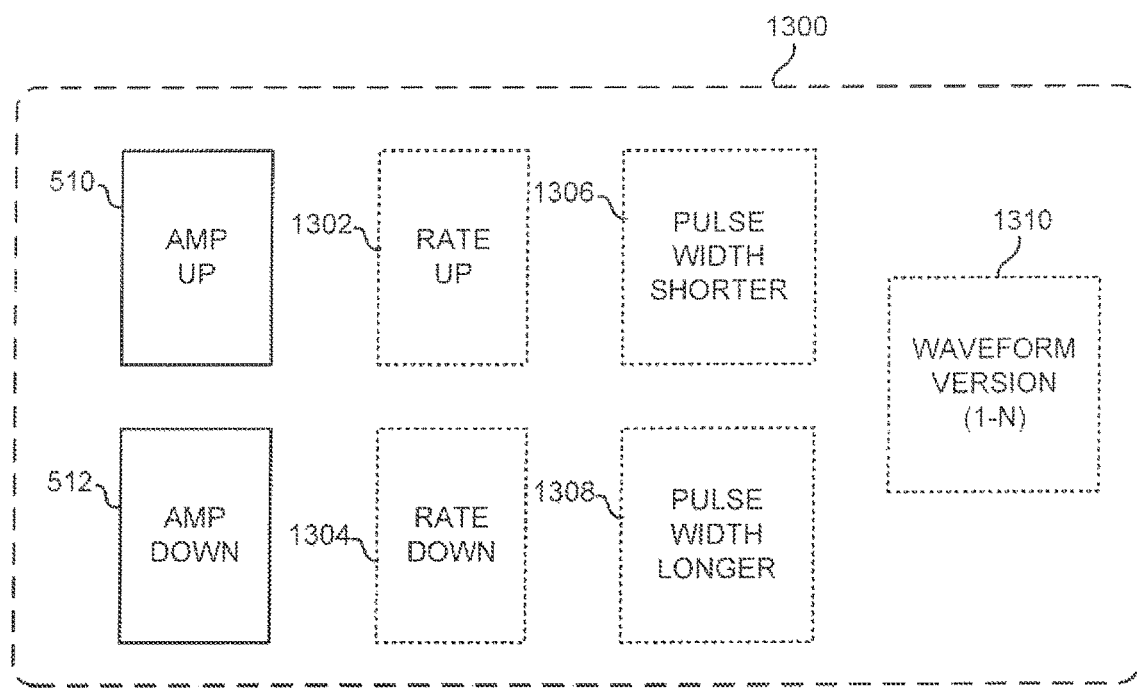
Figure 13

Figure 17

| | | |
|---|---|---|
| Amplitude: 2.0 V — 1704 | | Functional Threshold (FT) — 1706 |
| Patient Control (Lower + Upper limit): 1.8–2.8 V  FT + 1.0 volts (11 Steps) — 1708 | | |
| Electrode Configuration | 1710 Plus, Minus, Plus: Off | |
| Start Delay: — 1720 | 30 minutes | |
| Pause Time: — 1722 | 15 minutes | |
| Therapy Duration: — 1724 | 8 hours | Exhalation: — 1740 | -4 / -1 |
| Pulse Width: — 1730 | 90 μseconds | Inhalation: — 1742 | 0 / +1 |
| Frequency: — 1732 | 33 hertz | Off Period: — 1744 | 38 / 13 |
| Max Stim Time: — 1734 | 4 seconds | | |
| Invert Signal: — 1750 | No | | |

| Therapy is off | ⋅)) Turn On | John Doe  ID: 12456-78 | De-ID: MPLS-062 | Serial #: NCR— | X Exit |

Actions — 1804
- Record Thresholds — Not Performed — 1818
- Adjust Stimulation — ✓ Changes Made — 1820
- Adjust Sensing — Not Performed Reports — 1806
- Last session — 13 September 2013 — 1838
- Current Report Patient Details — 1808
- Physician — Dr. Sleep
- Implant Date — 13 Mar 2013
- Patient Details Patient Therapy Status — 1810
- Amplitude Change V   2.2 ▶ 2.3   [No patient change] [Patient made Change] — 1816, 1817
- Battery   Good
- Usage h   948 (37 hours per week)

Stimulation — 1830
- Amplitude V   2.0 (2.3) — 1832
- Patient Control V   1.8 – 2.2 (1.9 – 2.3) — 1834
- Start Delay m   30 — 1835
- Pause Time m   15 — 1836
- Therapy Duration h   8

Sensing — 1860
- Exhalation   –4 | –1
- Inhalation   0 | +1
- Off Period %   38
- Max stim Times   4
- Invert Signal   No 13 March 2014 17:10

Demonstration mode

Figure 21

SYSTEM AND METHOD OF MONITORING FOR AND REPORTING ON PATIENT-MADE STIMULATION THERAPY PROGRAMMING CHANGES

CROSS REFERENCE TO RELATED CASES

This application is a continuation of U.S. patent application Ser. No. 15/836,224, filed Dec. 8, 2017, which is a continuation of U.S. patent application Ser. No. 14/689,469, filed Apr. 17, 2015, now U.S. Pat. No. 9,839,786, which are hereby incorporated by reference in their entirety.

SUMMARY

Embodiments are directed to a programmer configured to effect communication with, and programming of, an implantable medical device configured to deliver neurostimulation therapy. The programmer comprises a display, such as touch screen display, and a processor comprising memory and coupled to the display. An interface is coupled to the processor and configured to receive therapy settings data indicative of current therapy settings operative in the implantable medical device and any modifications made to the therapy settings by a patient. The processor is configured to determine if one or more therapy settings have been modified since the last interaction with the patient, and coordinate displaying of the current therapy settings, the one or more therapy settings modified by the patient, and a previous state of the one or more therapy settings modified by the patient on the display.

Other embodiments are directed to a programmer configured to effect communication with, and programming of, an implantable medical device configured to deliver neurostimulation therapy. The programmer comprises a display, such as touch screen display, and a processor comprising memory and coupled to the display. An interface is coupled to the processor and configured to receive therapy settings data indicative of current therapy settings operative in the implantable medical device and any modifications made to the therapy settings by a patient. The interface is further configured to receive usage data indicating a duration of therapy delivered to the patient over a specified span of time. The processor is configured to determine if one or more therapy settings have been modified since the last interaction with the patient, and coordinate displaying of the current therapy settings, the one or more therapy settings modified by the patient, a previous state of the one or more therapy settings modified by the patient on the display, and the usage data on the display.

Further embodiments are directed to a method comprising receiving, at a programmer, therapy settings data acquired from an implantable medical device configured to deliver neurostimulation therapy. The therapy settings data comprises data indicative of current therapy settings operative in the implantable medical device and any modifications made to the therapy settings by a patient. The method also comprises determining, by the programmer, if one or more therapy settings have been modified by the patient. The method further comprises displaying, on a display of the programmer, the current therapy settings, the one or more therapy settings modified by the patient, and a previous state of the one or more therapy settings modified by the patient.

The above summary is not intended to describe each disclosed embodiment or every implementation of the present disclosure. The figures and the detailed description below more particularly exemplify illustrative embodiments

BRIEF DESCRIPTION OF THE DRAWINGS

Throughout the specification reference is made to the appended drawings, where like reference numerals designate like elements, and wherein:

FIG. 2A is an insert to the view of FIG. 2 and illustrates a neurostimulator implanted into the patient of FIG. 2;

FIG. 12 illustrates each of the representative parameters A, B, and C of FIGS. 10 and 11 superimposed on an illustrative stimulation waveform in accordance with various embodiments;

FIG. 13 illustrates a patient remote which includes control buttons for adjusting a number of different therapy parameters in accordance with various embodiments;

FIG. 17 is a screen of an application interface provided on a display of a programmer showing various therapy parameters of an implantable medical device, such as a neurostimulator, that can be adjusted by a clinician in accordance with various embodiments;

FIG. 18 is a screen of an application interface showing various therapy settings on a display of a programmer in accordance with various embodiments;

FIG. 21 is a screen of an application interface showing a summary report that provides a clear indication of the initial and final states of any therapy setting that was modified between the first and last programming sessions of a multi-programming session sleep study in accordance with various embodiments.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part of the description hereof and in which are shown by way of illustration several specific embodiments. It is to be understood that other embodiments are contemplated and may be made without departing from the scope of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Embodiments of the present disclosure are directed to an apparatus and method for monitoring for patient modification of one or more therapy settings of an implantable medical device and reporting any such patient modifications in a manner that is readily perceivable via a programmer. Other embodiments are directed to an apparatus and method for monitoring for patient modification and automatic (i.e., algorithmic) device-initiated modification of one or more therapy settings of an implantable medical device and reporting any such patient and automated device-initiated modifications in a manner that is readily perceivable via a programmer. In some embodiments, the programmer is a wireless programmer, such as a tablet configured to implement an application or browser. In other embodiments, the programmer may have a wired communications interface and be configured to implement an application or browser and communicate with an IMD via a multiplicity of communication links which can include one or more wireless communication links and/or one or more wired communication links.

Figure 1:
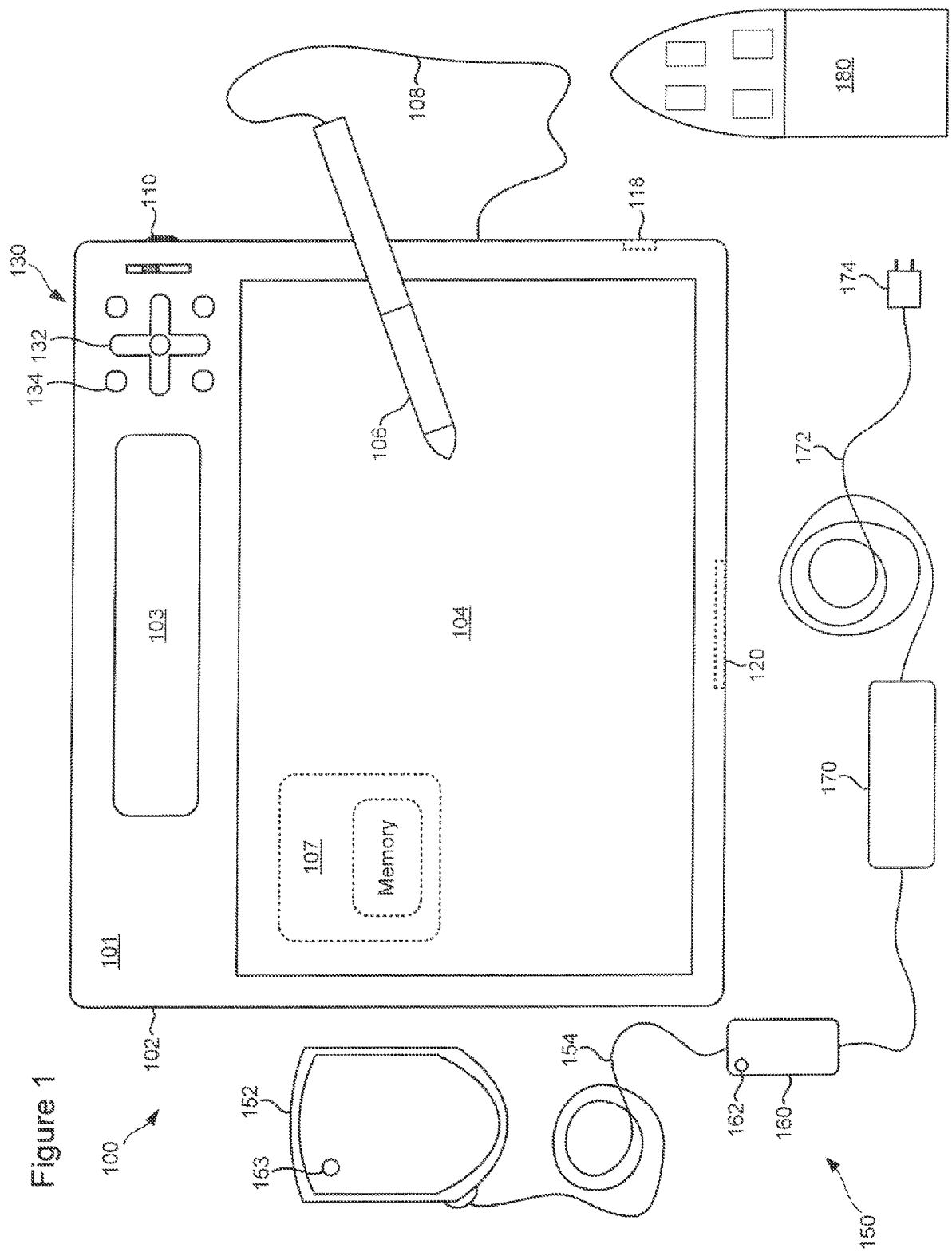
FIG. 1 shows apparatuses for effecting communication with an implantable medical device (IMD) in accordance with various embodiments.

FIG. 1 shows apparatuses for monitoring for patient modification of one or more therapy settings of an implantable medical device and reporting any such patient modifications in a manner that is readily perceivable. Some embodiments are directed to a wireless programmer, while others are directed to a wired programmer. For purposes of illustration and not of limitation, the following discussion primarily refers to a wireless programmer, it being understood that the embodiments disclosed herein can employ a wired programmer. The term wireless refers to a communication connection that includes at least one wireless link, although the communication connection can also include a wired link. FIG. 1 shows a wireless programmer 102 configured to communicate with a telemetry cable 150. According to various embodiments, the wireless programmer 102 can be implemented as a tablet computer or other mobile computing device (e.g., a notebook or laptop). The wireless programmer 102 is configured to implement an application (also referred to as an "app") or a browser that facilitates clinician interaction with the telemetry cable 150 and the IMD. The wireless programmer 102 can be used by a clinician to interrogate an IMD and make adjustments to various parameters of an IMD (referred to as "programming" the IMD), monitor therapy delivered by the IMD, and monitor patient adherence to prescribed therapy. FIG. 1 also shows a patient remote 180 configured to facilitate patient adjustment of one or more therapy settings of the IMD directly (i.e., without the need of programmer 102).

The telemetry cable 150 communicates wirelessly with the IMD and facilitates wireless communication between the IMD and the wireless programmer 102. Generally, each wireless programmer 102 is uniquely paired to a particular telemetry cable 150, and each wireless programmer 102 works only with its uniquely paired telemetry cable 150. In some embodiments, a generic portable computing device (e.g., a tablet or laptop) can be configured by software to serve as an "app-based" programmer, and can operate as a stand-alone programmer or in cooperation with a desktop or stationary programmer (e.g., PC programmer). App-based programmers can be uniquely paired to a particular telemetry cable at any given moment, but this pairing relationship can be changed on-the-fly as a sleep technician moves from his or her PC terminal to a tablet and for utilization by remote support individuals.

The wireless programmer 102 includes a display 104 and a stylus 106 which allows the clinician to interact with the display 104, such as by inputting, modifying, and reviewing data. The stylus 106 may be a double sided device, so that either the pen tip or the eraser site may be used. The stylus 106 is shown tethered to the programmer 102 via a cable 108, which provides signaling and power to the stylus 106. Alternatively, the stylus 106 may be a wireless device with its own power source, such as a battery. In some embodiments, the display 104 can be configured as a touchscreen, in which case the stylus 106 may be excluded or an optional accessory. A handle 103 is provided in the upper portion of the programmer 102, and a recessed section of the programmer housing 101 above or below the handle 103 can be used to store the stylus 106 when not in use.

The wireless programmer 102 includes a number of interfaces, buttons, and controls, several of which are shown in the illustrative embodiment of FIG. 1. A power button 110 is provided on an upper right edge of the housing 101, and a cluster of controls 130 is provided on an upper right portion of the front surface of the housing 102. The control cluster 130 includes a multi-position control 132 that allows the clinician to interact with a processor 107 and display 104 of the programmer 102 in various ways. The processor 107 of the programmer 102 can be programmed to implement the various processes and functions described herein. Additional buttons 134 can be situated proximate (or apart from) the control cluster 130. For example, the control cluster 130 and additional buttons 134 can allow the clinician to select between different operating modes and/or various user-assignable or emergency-off functions (e.g., places the IMD into a known safe state or performs live-saving functions). The wireless programmer 102 includes a number of different interfaces/components including a power connector plus USB port 118 and a network cable and USB port 120. The interfaces and components listed above are for purposes of illustration, not of limitation.

The telemetry cable 150 is configured to wirelessly communicate with both the wireless programmer 102 and an IMD. The telemetry cable 150 effectively serves as a wireless bridge or modem between the programmer 102 and the IMD. The telemetry cable 150 comprises disparate communication devices that together support a communication channel comprising disparate sequential communication links configured to facilitate bidirectional communication between the IMD and the wireless programmer 102. In particular, the telemetry cable 150 provides for bi-directional communication with the IMD and bi-directional communication with the wireless programmer 102. According to various embodiments, the wireless programmer 102 monitors for establishment of, and loss of connectivity with, each of the disparate communication links that define the hybrid communication channel. In some embodiments, the telemetry cable 150 is configured to self-monitor its connectivity with the wireless programmer 102 and to indicate a status of said connectivity. In some embodiments, the telemetry cable 150 is configured to deliver power to the IMD in addition to communicating with it (e.g., via inductive coupling). The IMD may use the wireless power to operate a portion or all of its functions or to recharge the IMD battery or capacitor.

In accordance with the embodiment shown in FIG. 1, the telemetry cable 150 includes a telemetry head 152 configured to wirelessly communicate with the IMD via a near-field link. The telemetry head 152 is shown to include a status indicator 153, such as an LED indicator. The telemetry head 152 can be configured to self-monitor establishment and loss of connectivity with the wireless programmer 102. Alternatively, or in addition, the telemetry head 152 can be configured to self-monitor establishment and loss of connectivity with the IMD. For example, the status indicator 153 can be illuminated with a green color to indicate good signaling between the telemetry head 152 and the IMD. The status indicator 153 can be illuminated with an orange color to indicate poor or no signaling between the telemetry head 152 and the IMD.

In some embodiments, the telemetry head 152 is configured to inductively communicate with the IMD via a near-field link. A near-field link appropriate for effecting communications with an IMD typically has a range of about 5 centimeters. A typical inductive near-field link between the telemetry head 152 is highly directional, operates safely through human tissue, and is susceptible to electrical noise. In addition to being extremely short range, inductive telemetry communication is low-power and does not interfere with medical or communication equipment. However, inductive telemetry signals are susceptible to electrical noise, such as from hospital beds, smart phones, tube monitors/TVs, power supplies, respiratory inductive plethysmography (RIP), RIP belts, the RIP box, PSG wires, and the head box, for example. In some embodiments, an alternative to near-field inductive communication can be implemented, including: e-field communications (MICS, ISM), and medium range induction technology which utilizes advanced amplifiers and transmitters to achieve ranges of up to 1 m. It is noted that the use of multiple coils, such as in three-axes implementations, can eliminate the directionality issue with inductive links.

A cable 154 extends from the telemetry head 152 and is connected to a wireless transceiver 160. The wireless transceiver 160 may be configured for short-range radio frequency (RF) communication. For example, the wireless transceiver 160 may be configured to implement a short-range RF communication link, such as by implementing a Bluetooth® (short-wavelength UHF radio waves in the ISM band from 2.4 to 2.485 GHz) or ZigBee® (radio waves in ISM radio bands: 868 MHz in Europe, 915 MHz in the USA and Australia, and 2.4 GHz in most jurisdictions worldwide) communications protocol. In some embodiments, the wireless transceiver 160 can be configured to wirelessly communicate with existing network infrastructure via an appropriate RF communication protocol, such as Wi-Fi® (also considered a short-range RF communication link of up to about 45 meters indoors). In such embodiments, a hybrid communication link can be established between the IMD and the wireless programmer 102 using a wireless local area network (WLAN) via a wireless network connection for increasing the wireless communication range of the telemetry cable 150.

The wireless transceiver 160 typically has a range significantly greater than that of the link established by the telemetry head 152 (e.g., on the order of at least a magnitude difference). For example, the wireless transceiver 160 may have a range of about 5-20 meters. In contrast to the near-field link described above, a typical wireless link established between the wireless transceiver 160 and wireless programmer 102 is not directional and is blocked by human tissue. Moreover, a wireless transceiver 160 implemented according to a Bluetooth® protocol operates at the same frequencies as Wi-Fi® and is ubiquitous and safe for use in hospitals and care facilities.

The wireless transceiver 160 is shown to include a status indicator 162. The wireless transceiver 160 can be configured to self-monitor establishment and loss of connectivity with the wireless programmer 102. Alternatively, or in addition, the wireless transceiver 160 can be configured to self-monitor establishment and loss of connectivity with the telemetry head 152. In some implementations, the status indicator 162 includes an LED, which indicates a good or nominal operating status by way of constant LED illumination. The status indicator 162 may blink or be extinguished to indicate a poor or non-operating status of the wireless transceiver 160. Power is supplied to the telemetry cable 150 by way of a power supply 170, which is shown to include a power cable 172 terminated by a standard AC wall plug 174. The power supply 170 provides power for both the wireless transceiver 160 and the telemetry head 152.

The wireless remote 180 is shown to include buttons to allow the patient to modify therapy parameters, and status indicators for implantable device status (e.g., remote and implantable device communication status and implantable device battery status) and remote status (remote battery status). The wireless remote 180 is utilized by a patient during home use of the therapy and to make necessary adjustments of therapy parameters if needed or desired.

Figure 2:
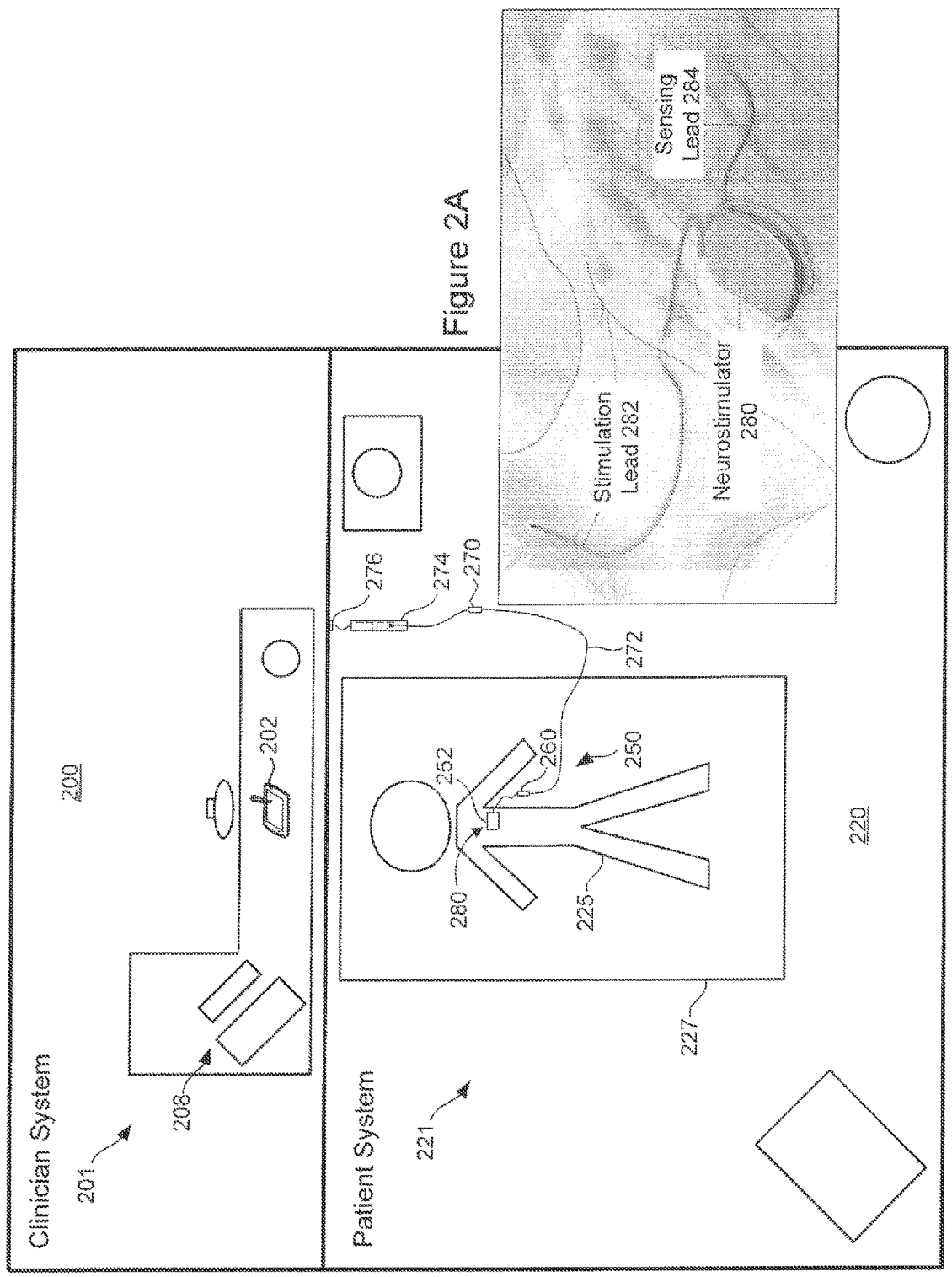
FIG. 2 is an illustration of a clinic or hospital equipped to monitor a patient during a medical evaluation, such as a sleep study for determining whether the patient is suffering from a sleep disorder, in accordance with various embodiments.

FIG. 2 is an illustration of clinic or hospital rooms equipped to monitor a patient 225 during a medical evaluation, such as a sleep study for determining whether the patient is suffering from a sleep disorder. In this illustrative embodiment, a neurostimulator 280 (see also FIG. 2A) has been implanted in the patient 225 in the subclavian region for purposes of treating obstructive sleep apnea. Obstructive sleep apnea is a common disorder, characterized by recurrent narrowing and closure of the upper airway accompanied by intermittent oxyhemoglobin desaturation and sympathetic activation. The onset of apnea is accompanied by a reduction in drive to the upper-airway muscles, and upper-airway patency is strongly correlated with the activation of the genioglossus muscle. Upper-airway stimulation with the use of unilateral stimulation of the hypoglossal nerve, synchronous with ventilation, is a viable treatment option, providing significant and clinically meaningful reductions in the severity of obstructive sleep apnea and self-reported sleepiness and improvements in quality-of-life measures.

The neurostimulator 280 shown in FIG. 2 includes a stimulation lead 282 that extends from the housing of the neurostimulator 280 to the hypoglossal nerve in the patient's neck. A sensing lead 284 extends from the housing of the neurostimulator 280 and is implanted at an intercostal muscle location of the rib cage. The sensing lead 284 detects intercostal muscle movement during patient respiration, signals from which are used to detect patient respiration. A pulse generator in the neurostimulator 280 provides electrical stimulation to the hypoglossal nerve via the stimulation lead 282 based on detected patient respiration.

In the illustrative testing environment shown in FIG. 2, the patient 225 is shown lying down on a bed 227 in a patient room 220 for purposes of conducting a sleep study. The patient room 220 may be configured and decorated much like a typical motel room to simulate a restful bedroom environment. FIG. 2 also shows a clinician room 200 which is typically a separate room adjacent to or near the patient room 220. The clinician room 200 is typically close to the patient room 220 to facilitate efficient evaluation of, and communication with, the patient 225 during the sleep study. Importantly, the clinician room 200 is separated by a wall or other privacy structure that provides a measure of privacy and security for the patient 225 during the sleep study. Although the presence of a walled structure between the clinician and patient rooms 200 and 220 advances the objective of enhancing the sleep environment for the patient's benefit, the walled structure presents a physical barrier between diagnostic equipment distributed between the physically separate clinician and patient rooms 200 and 220.

In the illustrative embodiment shown in FIG. 2, a patient system 221 is situated in the patient room 220 and a clinician system 201 is situated in the clinician room 200. The patient system 221 includes a telemetry cable 250 positioned proximate the patient 225, and includes a telemetry head 252 communicatively coupled to a wireless transceiver 260. The patient system 221 may also include a patient remote (not shown) that enables the patient to modify one or more therapy settings of the IMD. Although a patient remote is a component of the system illustrated in FIG. 2, the patient remote may be excluded from the sleep study/therapy titration scenario represented in FIG. 2. The telemetry cable 250 is connected to a power supply 270 via a power cable 272. The power supply 270 is shown connected to a AC power strip 274 which, in turn, is electrically connected to a standard AC wall socket 276. The clinician system 201 includes a wireless programmer 202, which is shown resting on a work desk within the clinician room 200. A computer system 208 and other equipment may be provided in the clinician room 200. The wireless programmer 202 situated within the clinician room 200 is communicatively coupled to the neurostimulator 280 via the telemetry cable 250. The wireless programmer 202 can be used by a clinician to interact with the neurostimulator 280 without disturbing the patient's sleep, which is important for conducting productive sleep studies.

Figure 3:
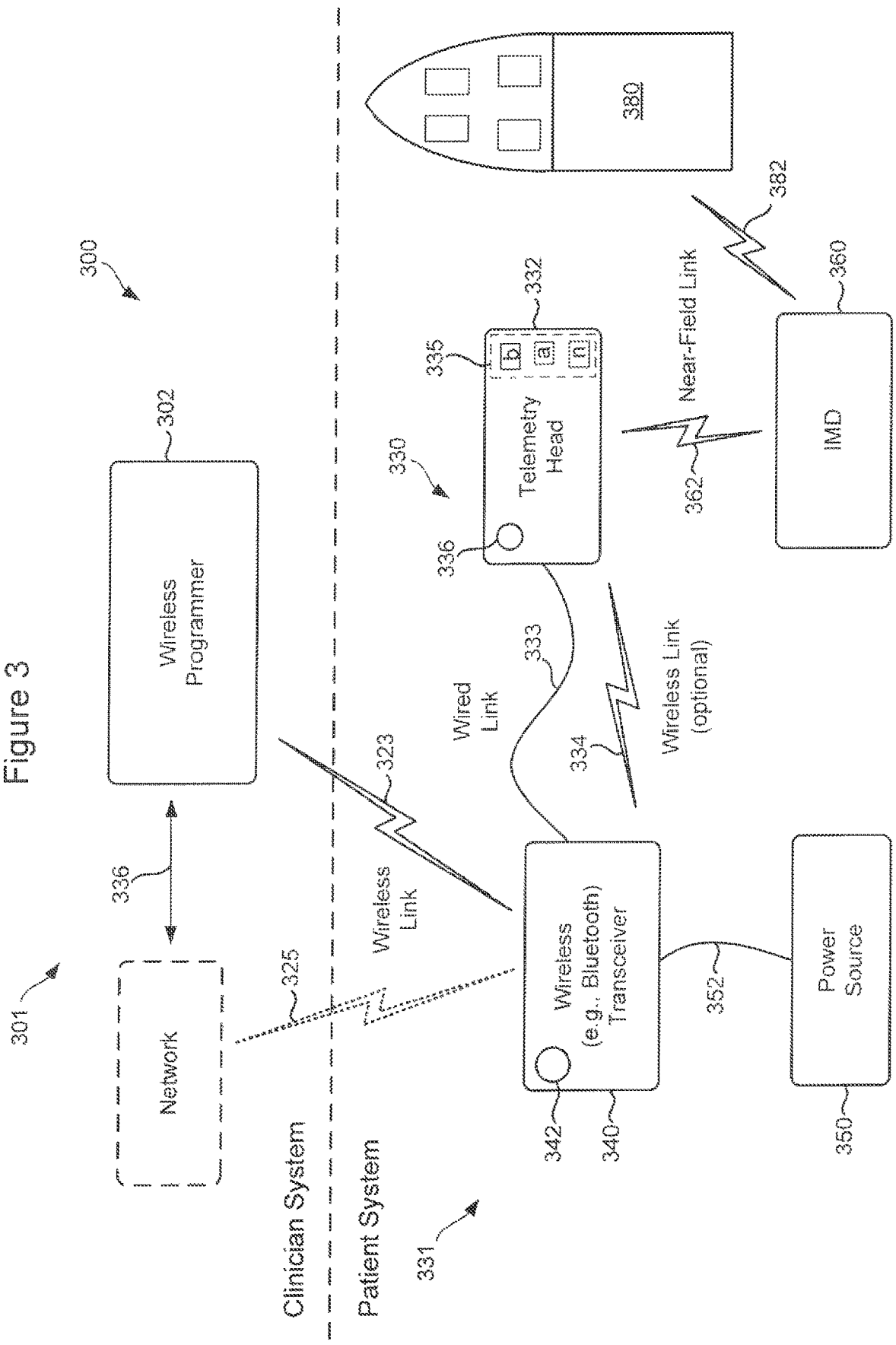
FIG. 3 illustrates an apparatus for effecting communication with an IMD in accordance with various embodiments.

FIG. 3 illustrates an apparatus for monitoring for patient modification of one or more therapy settings of an IMD and reporting any such patient modifications in a manner that is readily perceivable in accordance with various embodiments. In the embodiment illustrated in FIG. 3, the apparatus 300 includes a wireless programmer 302 configured to communicate with an IMD 360, such as a neurostimulator for treating obstructive sleep apnea, via a wireless communication channel comprising disparate communication links, including a wireless link 323 and a near-field link 362. The wireless programmer 302 is illustrated as a component of the clinician system 301 that can be operated from a room adjacent to or near a room within which a patient system 331 is situated. The patient system 331 includes a patient remote 380 configured to facilitate patient adjustment of one or more therapy settings of the IMD directly (i.e., without the need of programmer 302) via a wireless communication link 382. The patient system 331 further includes a telemetry cable 330 having a telemetry head 332 communicatively coupled to a wireless transceiver 340, such as a Bluetooth® or ZigBee® transceiver. The telemetry head 332 communicates with the IMD 360 via a separate wireless link, shown as a near-field link 362. In some implementations, the near-field link 362 can be an inductive communication link.

In one implementation, a wired link 333 communicatively couples the telemetry head 332 with the wireless transceiver 340. In other implementations, a wireless link 334 can be implemented to communicatively couple the telemetry head 332 with the wireless transceiver 340. The telemetry head 332 can include a status indicator 336, which provides a visual indication of the operating status of the telemetry head 332. The telemetry head 332 can include a user control facility 335 to allow user adjustment of one or more telemetry device functions. According to some embodiments, the user control facility 335 allows the clinician to control basic operations of the telemetry device 332 without need of the full programmer interface. Utilization of these controls 335 includes allowing a clinician quick access to basic controls of the telemetry device 332 when in the patient's room, as well as allowing the same control of the telemetry device 332 by the patient in some embodiments. For example, the user control facility 335 may include a number of control buttons (e.g., buttons a-n) that are actuatable by the clinician and control various basic operations of the telemetry device 332. Button 335-a, for example, can be an on/off switch that respectively enables and disables manual adjustment of one or more functions of the telemetry device 332. Button 335-b can be a variable rocker switch that allows the clinician to gradually (e.g., step-wise) increase and decrease the strength of the wireless (e.g., inductive) link between the telemetry device 332 and the implantable medical device 360. Button 335-n can be a switch that initiates a self-diagnostic test that assesses the present ability of the telemetry device 332 to communicatively interface with the IMD 360. Other buttons may be provided to effectuate desired operations and/or functionality. For example, button 335-n can be an emergency button that places the IMD 360 into a known safe mode or causes the IMD 360 to perform a life-saving function. The emergency button 335-n may, for example, turn a neurostimulator off, return a pacemaker to a basic mode, or disable a defibrillation capability of an ICD (implantable cardioverter/defibrillator).

The wireless transceiver 340 can include a status indicator 342, which provides a visual indication of the operating status of the transceiver 340. A power source 350 is shown coupled to the wireless transceiver 340 via a wired power cable 352. The power source 350 provides power to both the wireless transceiver 340, via the power cable 352, and to the telemetry head 332, via the wired link 333. In some implementations, the power source 350 is configured to connect with a standard AC wall socket. In other implementations, the power source 350 may be a battery or other self-contained power source. In implementations that use a wireless link 334 between the telemetry head 332 and wireless transceiver 340, the telemetry head 332 may include its own power source, such as a battery.

Figure 4:
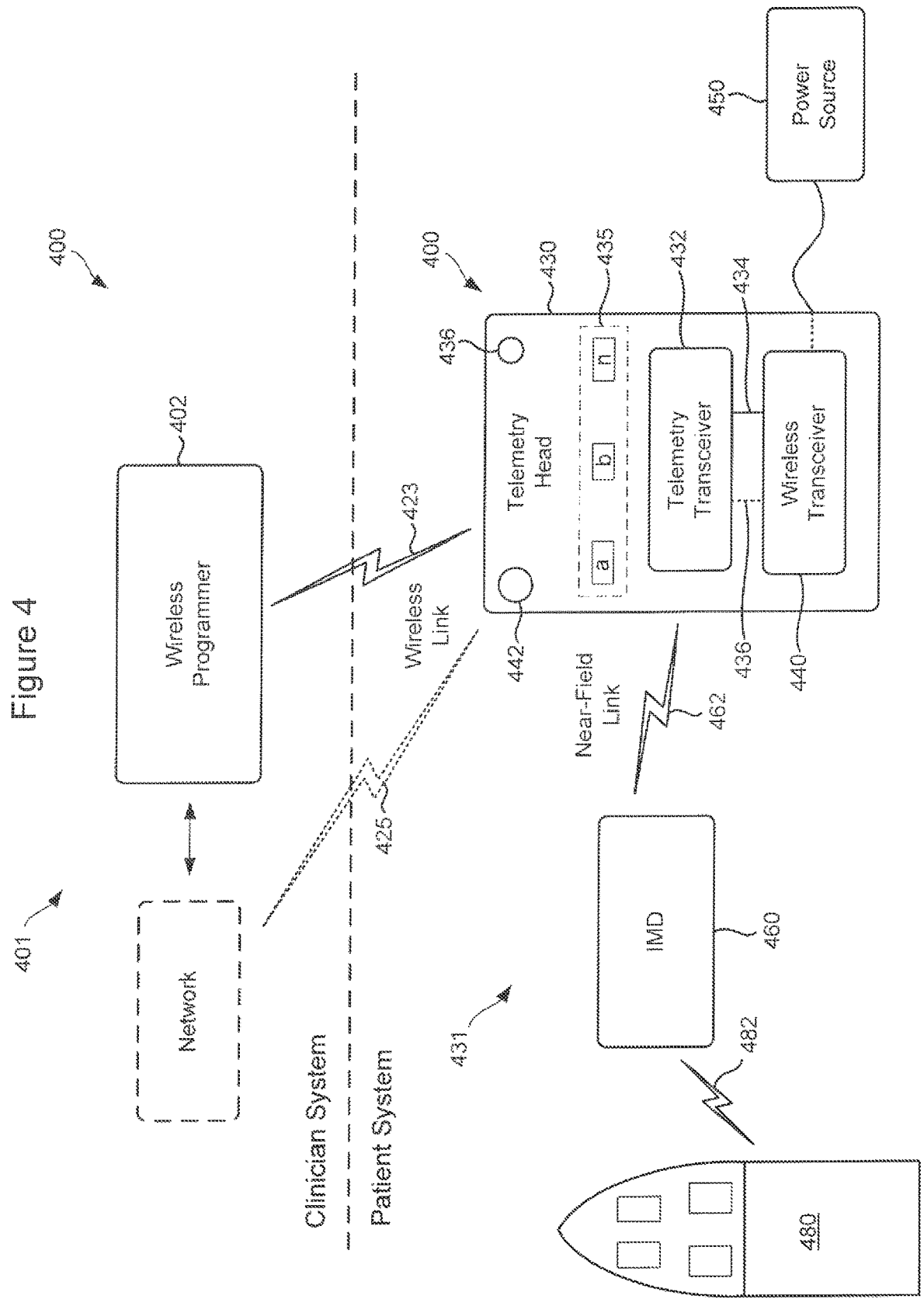
FIG. 4 illustrates an apparatus for effecting communication with an IMD in accordance with various embodiments.

FIG. 4 illustrates an apparatus for monitoring for patient modification of one or more therapy settings of an IMD and reporting any such patient modifications in a manner that is readily perceivable in accordance with other embodiments. In the embodiment illustrated in FIG. 4, the apparatus 400 includes a wireless programmer 402 configured to communicate with an IMD 460 (e.g., a neurostimulator for treating obstructive sleep apnea) via a wireless communication channel comprising disparate communication links, including a wireless link 423 and a near-field link 462. The wireless programmer 402 is illustrated as a component of the clinician system 401 that can be operated from a room adjacent to or near a room within which a patient system 431 is situated. In the embodiment shown in FIG. 4, the patient system 431 includes a patient remote 480 configured to facilitate patient adjustment of one or more therapy settings of the IMD 460 directly (i.e., without the need of programmer 402) via a wireless communication link 482. The patient system 431 also includes a telemetry device or apparatus 400 configured to wirelessly communicate with both the wireless programmer 402 and the IMD 460 using different wireless communication links. The telemetry device 400 shown in FIG. 4 integrates into a single device a telemetry transceiver 432 and a wireless transceiver 440.

The telemetry transceiver 432 is configured to establish a near-field wireless link 462 with the IMD 460. The wireless transceiver 440 is configured to establish a short range RF communication link with the wireless programmer 402 (e.g., via a Bluetooth® or ZigBee® protocol). The wireless transceiver 440 is communicatively coupled to the telemetry transceiver 432 via a signaling channel 434. In one implementation, a power connection 436 couples power supplied by a power source 450 from the wireless transceiver 440 to the telemetry transceiver 432. In another implementation, the power source 450 supplies power to the wireless transceiver 440 and the telemetry transceiver 432 individually. According to some embodiments, the telemetry transceiver 432 and the wireless transceiver 440 constitute discrete components of the telemetry device 400. In other embodiments, the telemetry transceiver 432 and the wireless transceiver 440 are implemented as components of a common integrated circuit or otherwise populating a common printed circuit board, with conductive traces provided for communicating data signals and power thereto and/or therebetween.

The telemetry device or apparatus 400 can include a user control facility 435 to allow user adjustment of one or more telemetry device functions. According to some embodiments, the user control facility 435 allows the clinician to control basic operations of the telemetry device 432 without need of the full capabilities of the programmer 402. As was previously discussed, utilization of these controls 435 includes allowing a clinician quick access to basic controls of the telemetry device 432 when in the patient's room, as well as allowing the same control of the telemetry device 432 by the patient in some embodiments. For example, the user control facility 435 may include a number of control buttons (e.g., buttons a-n) that are actuatable by the clinician and control various basic operations of the telemetry device 432. Buttons 435-a, 435-b, and 435-n, for example, can have the same or different functionality as described above with reference to controls 335a-n shown in FIG. 3. Other buttons may be provided to effectuate desired operations and/or functionality.

Figure 5A:
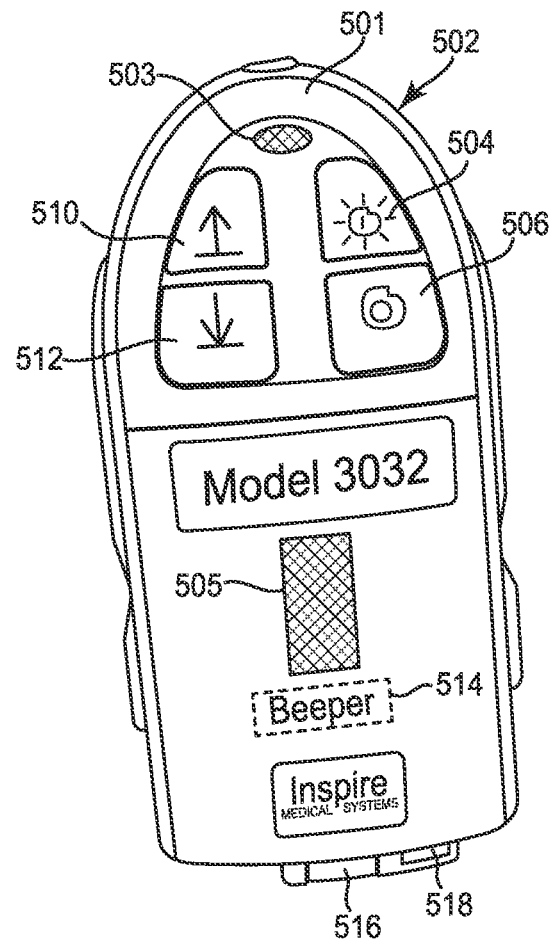
FIGS. 5A and 5B illustrate front and rear views of a patient remote in accordance with various embodiments.
Figure 5B:
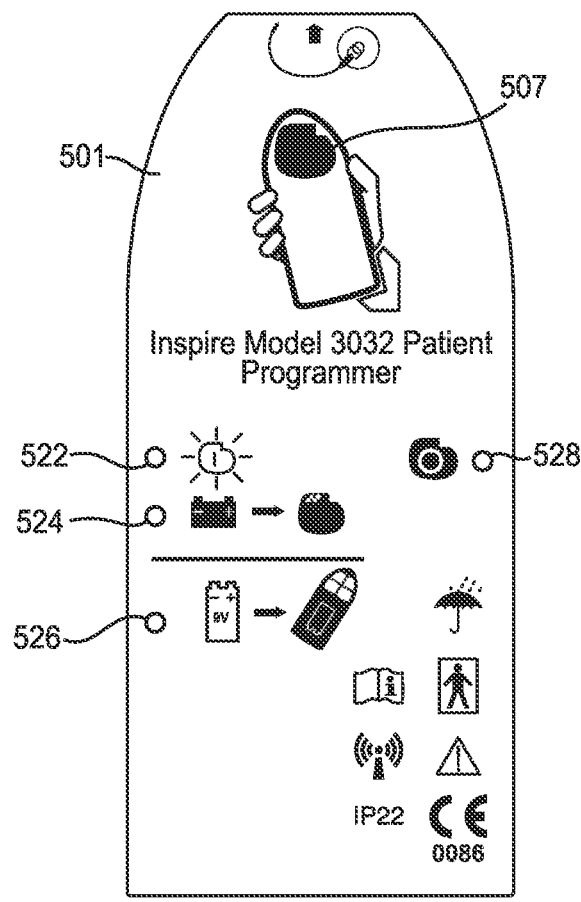

FIGS. 5A and 5B illustrate front and rear views of a patient remote in accordance with various embodiments. The patient remote 501 shown in FIG. 5A has a control panel 502 which includes a number of user actuatable control buttons. The control buttons provided on the control panel 502 allow the patient to turn therapy on and off, pause therapy, and allow the patient to adjust one or more parameters that affect the operation of the implantable medical device that is surgically implanted in the patient. The number and type of control buttons provided on the control panel 502 are purposefully few and simple in operation with limited functionality. In the embodiment of the patient remote 501 shown in FIG. 5A, the control panel 502 includes a therapy ON button 504 and a therapy OFF button 506, which can be actuated to respectively turn on and off stimulation therapy by the patient. The control panel 502 further includes an increase control 510, which allows the patient to increase stimulation strength within a range selected by the clinician. A decrease control 512 provided on the control panel 501 allows the patient to decrease the stimulation strength within a range pre-selected by the clinician.

According to some embodiments, the patient remote 501 includes a beeper 514, which provides audio feedback to the patient while performing patient programming of the implanted medical device. In other embodiments, the patient remote 501 includes one or both of a microphone 503 and an oximetry sensor 505. Although shown on the front cover of the patient remote 501, the oximetry sensor 505 can be situated elsewhere on the patient remote 501 (e.g., on the rear or side exterior surface or an interior surface exposed by removal of the front cover). The microphone 503 can also be mounted elsewhere on the patient remote 501. The microphone 503 can be used to detect respiratory noise, such as snoring, which can be analyzed by circuitry within the patient remote 501. For example, the circuitry can be configured to determine maximum nocturnal sound intensity (dBmax) and/or to produce a snoring index (SI) (i.e., the number of snores per hour of sleep). The oximetry sensor 505 can be configured to facilitate pulse oximetry on a patient's finger that is placed on the sensor 505. Circuitry within the patient remote 501 can be configured to determine the patient's oxygen saturation. The circuitry can also be configured to calculate the oxygen desaturation index or ODI of the patient, by calculating the number of times per hour of sleep that the patient's blood oxygen level drops by 3 percent or more from baseline. Respiratory noise and/or oximetry (e.g., ODI) data can be used to assess effectiveness of therapy setting changes made by the patient or automatically. The patient remote 501 may also include an accelerometer or motion sensor (not shown), and circuitry can be configured to detect and monitor patient movement during sleep. Also shown along a lower peripheral edge of the patient remote 501 is a release button 516, which allows access to an interior compartment of the patient remote that houses a battery. A wrist strap attachment 518 allows for the addition of a convenient wrist strap to enhance portability of the patient remote 501.

FIG. 5B shows a rear surface of the patient remote 501, which includes various types of information useful to the patient as well as a number of illuminatable indicators. Among the various types of information provided on the rear surface of the patient remote 501 is an illustration of a target 507. The target 507 indicates the location of the patient remote 501 to be positioned above the IMD surgically implanted within the patient when communicating. The various indicators include a therapy ON indicator 522, which illuminates in green to indicate that therapy is presently on. A therapy OFF indicator 528 illuminates in yellow to indicate that therapy is presently off. Typically, the therapy OFF indicator 528 turns on after the patient presses a button on the control panel 502 other than the therapy ON button 504. In some cases, neither the therapy ON or therapy OFF indicators 522 and 528 turn on after pressing any button. In such cases, this indicates that the patient remote 501 did not communicate with the IMD.

In the embodiment shown in FIG. 5B, a stimulator battery status indicator 524 becomes illuminated in various ways to communicate different information after any control button on the control panel 502 is pressed. For example, the stimulator battery status indicator 524 illuminates green (constant illumination) to indicate that the battery of the IMD is good. When the stimulator battery is low, the green stimulator battery status indicator 524 blinks after any button on the control panel 502 is pressed. The blinking green indicator 524 indicates to the patient that a call to the clinician's office is required. In cases where the green stimulator battery status indicator 524 is off after pressing any button on the control panel 502, this indicates that the patient remote 501 did not communicate with the IMD.

The embodiment shown in FIG. 5B includes a battery indicator 526, the state of which communicates various types of information about the status of the patient remote's battery. The battery indicator 526 turns on with constant illumination after any button on the control panel 502 is pressed. A constant illumination state of the battery indicator 526 indicates that the patient remote 501 is operating properly. When the patient remote's battery is low, the battery indicator 526 blinks after any button on the control panel 501 is pressed. If the battery indicator 526 is off after pressing any button on the control panel 502, immediate replacement of the patient remote's battery is required. According to some embodiments, usage data and therapy settings can allow for more accurate predictions of remaining IMD battery life made by the programmer or patent remote.

Figure 6:
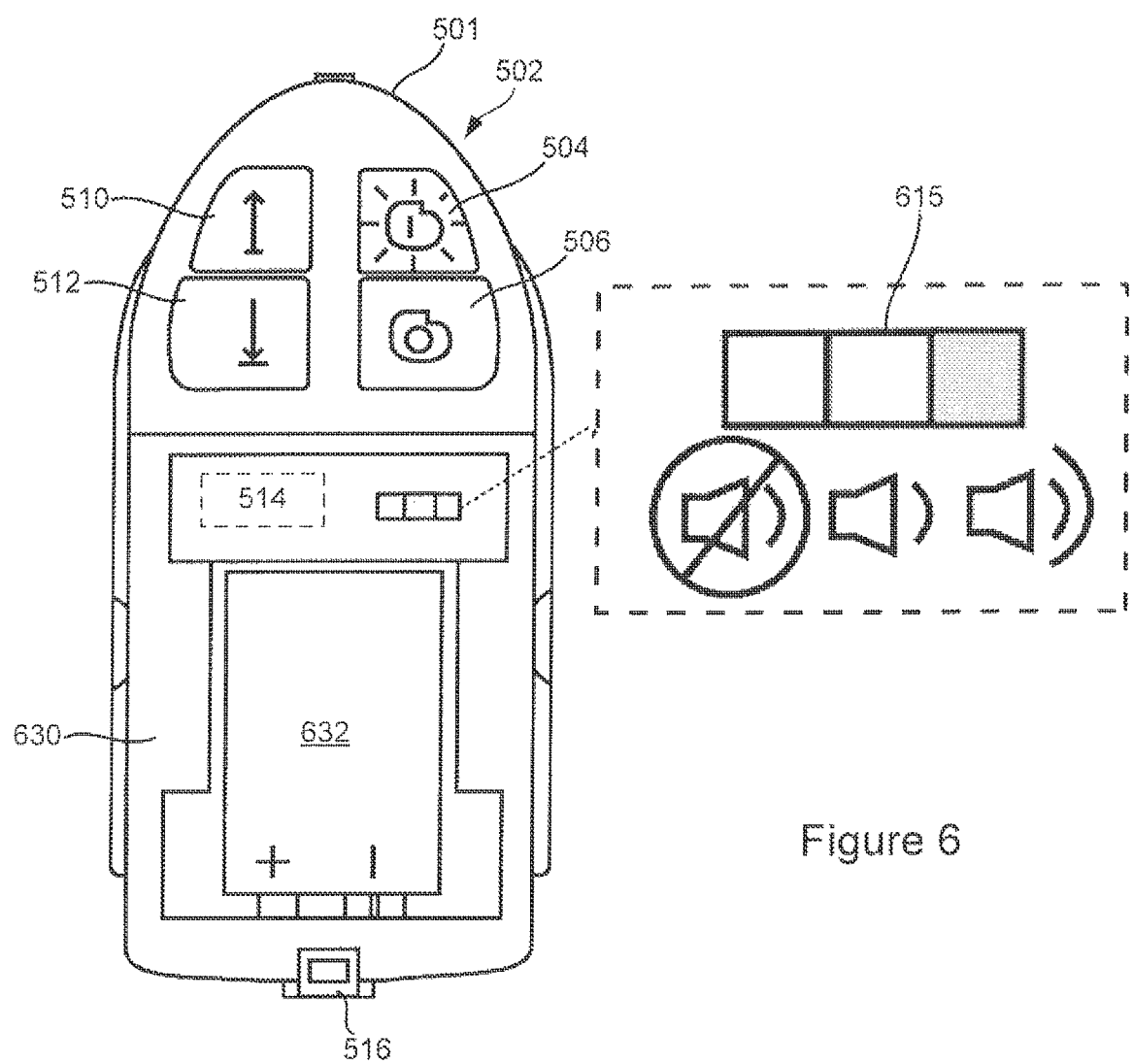
FIG. 6 shows a patient remote with its front cover removed in accordance with various embodiments.

FIG. 6 shows a patient remote 501 with its front cover removed in accordance with various embodiments. The front cover of the patient remote 501 can be removed by actuation of the release button 516. Removing the front cover allows access an internal compartment 630 that houses the battery 632, which is typically a 9 V battery. A beeper 514 and a beeper control 615 are shown in the compartment 630 underneath the patient remote's front cover. The beeper 514 includes a speaker and driver electronics which are coupled to the beeper control 615. The beeper control 615 allows the user to adjust the volume of the beeper, such as between three different amplitude states as shown in FIG. 6. Generally, the beeper volume is set too high as a default.

The beeper is used to facilitate patient programming of the IMD and provides auditory feedback during the programming process. During a targeting mode (i.e., properly positioning the patient remote 501 above the IMD), for example, the beeper is used much like a stud finder is used for locating structures within walls, to locate the best position for communicating with the IMD. During a targeting mode of operation, the patient presses the therapy OFF button 506 and moves the patient remote 501 in proximity with the IMD that is surgically implanted within the patient. The patient continues to hold the therapy OFF button 506 while moving the patient remote 501 until a continuous beep from the beeper 514 is heard. When the beeper transitions from a discontinuous beep to a continuous beep, the patient has found the best location for programming the IMD. The patient may then release the therapy OFF button 506, and if desired, turn therapy on again via the therapy ON button 504.

The beeper 514 can be used for other procedures, such as when turning on and off therapy via the control buttons 504 and 506, respectively. When the patient wishes to turn on therapy, the patient remote 501 is positioned over the stimulator and the therapy ON button 504 is pressed. If the beeper volume is on, a beep confirms the programming change. It is noted that the stimulation turns on with the same stimulation strength that was set when the patient turned therapy off. When therapy is turned on, the patient will feel one burst of stimulation. Therapy is then delayed for a set period of time while the patient falls asleep. This delay is called the start delay (or therapy delay). The patient can check to see if the therapy ON indicator 522 is constantly illuminated. If the green indicator 522 is constantly illuminated, therapy was successfully turned on. The therapy on indicator 522 remains on for about six seconds after the therapy ON button 504 is released. The beeper 514 is activated when turning therapy off. For example, the patient can position the patient remote 501 over the IMD, and then press the therapy OFF button 506. If the deeper volume is on, a beep confirms this programming change. The therapy OFF indicator 528 should now be illuminated on the back of the patient remote 501. If the yellow indicator 528 is on, the therapy was successfully turned off. This indicator 528 remains on for about six seconds after the therapy OFF button 506 is released.

The increase and decrease stimulation buttons 510 and 512 of the control panel 502 allow the patient to respectively increase and decrease the stimulation strength (amplitude) within a range previously selected (programmed) by the clinician. The strength of hypoglossal stimulation, for example can be modified by the patient within a stimulation range pre-programmed by the clinician in order to enhance patient comfort while providing efficacious therapy to the patient. If stimulation feels too strong, the patient may decrease the stimulation strength by pressing the decrease stimulation strength button 512. If no or little stimulation is felt by the patient, the patient may wish to increase the stimulation strength by pressing the increase stimulation strength button 510.

According to one illustrative patient programming routine, the patient positions the patient remote 501 over the IMD, and presses the therapy ON button 504. It is noted that therapy must be on in order to increase stimulation strength according to various embodiments. The patient may increase or decrease stimulation strength by pressing the increase and decrease stimulation strength buttons 510 and 512, respectively. To evaluate the stimulation strength adjustment, the patient turns off therapy using the therapy OFF button 506. The patient then turns on therapy using the therapy ON button 504. One burst of stimulation is delivered to the patient when therapy is turned on to indicate the relative strength of the stimulation energy being delivered to the patient. The beeper 514 beeps once for each successful adjustment. If the patient remote beeps rapidly three times, the patient has reached the stimulation strength adjustment limit, which includes both upper and lower limits.

Figure 7:
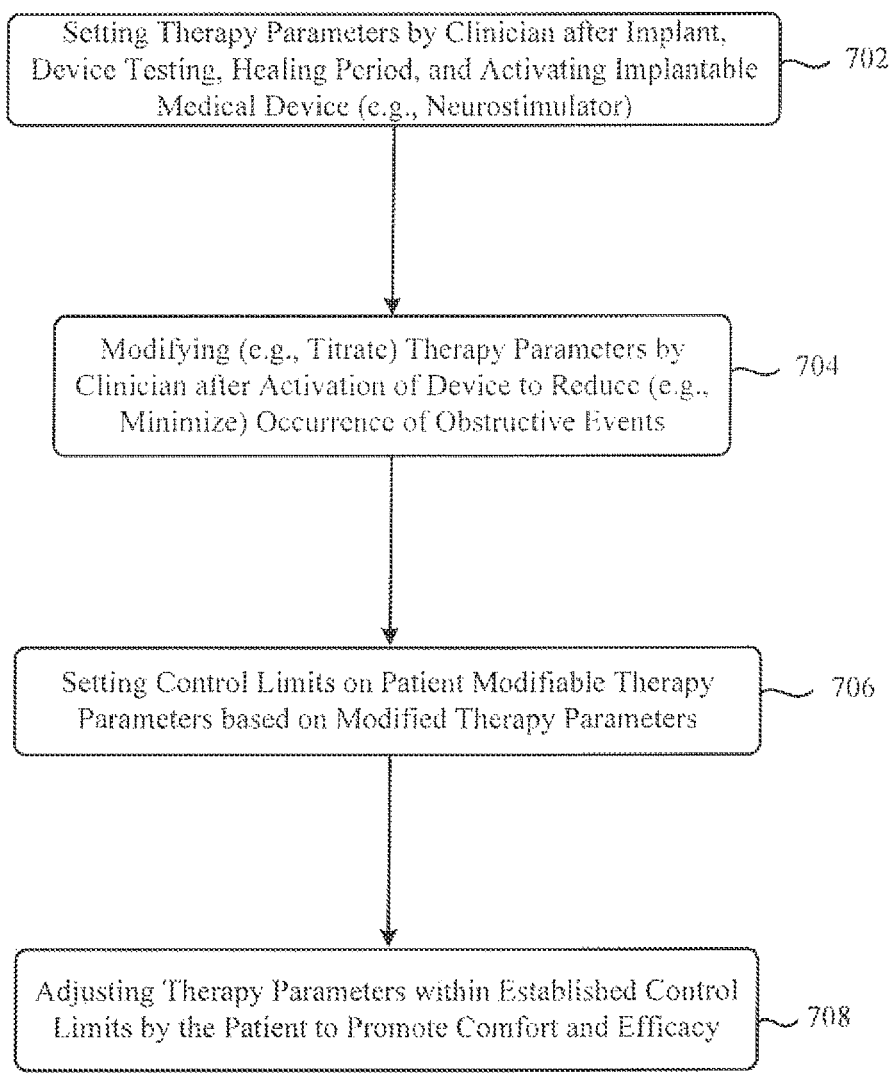
FIG. 7 illustrates various processes for adjusting therapy parameters of an implantable medical device using a patient remote in accordance with various embodiments.

FIG. 7 illustrates various processes for adjusting therapy parameters of an IMD using a patient remote in accordance with various embodiments. For purposes of illustration and not of limitation, the methodology shown in FIG. 7 will be described within the context of a neurostimulator device configured to treat obstructive sleep apnea. It is understood that the processes shown in FIG. 7 and other figures can apply to other IMDs that deliver therapy, such as a cardiac pacemaker, resynchronizer, cardioverter/defibrillator, muscle stimulator or other type of stimulation device. The method embodiment shown in FIG. 7 involves setting 702 therapy parameters of an IMD, such as a neurostimulator, by a clinician after implant/device testing and subsequent to a healing period, followed by activating the neurostimulator after device testing. The methodology shown in FIG. 7 also involves modifying 704 (e.g., titrating) therapy parameters of the neurostimulator by the clinician after activation of the device to reduce (e.g., minimize) occurrence of obstructive events. In addition to titrating the therapy parameters of the neurostimulator, the method of FIG. 7 involves setting 706 control limits on patient modifiable therapy parameters based on the therapy parameters titrated (i.e., modified) in step 704. The methodology of FIG. 7 further involves adjusting 708 therapy parameters within the established control limits by the patient to promote comfort and efficacy of the therapy delivered by the neurostimulator. Adjusting 708 the therapy parameters within the control limits established by the clinician involves use of a patient remote of a type described herein.

Figure 8:
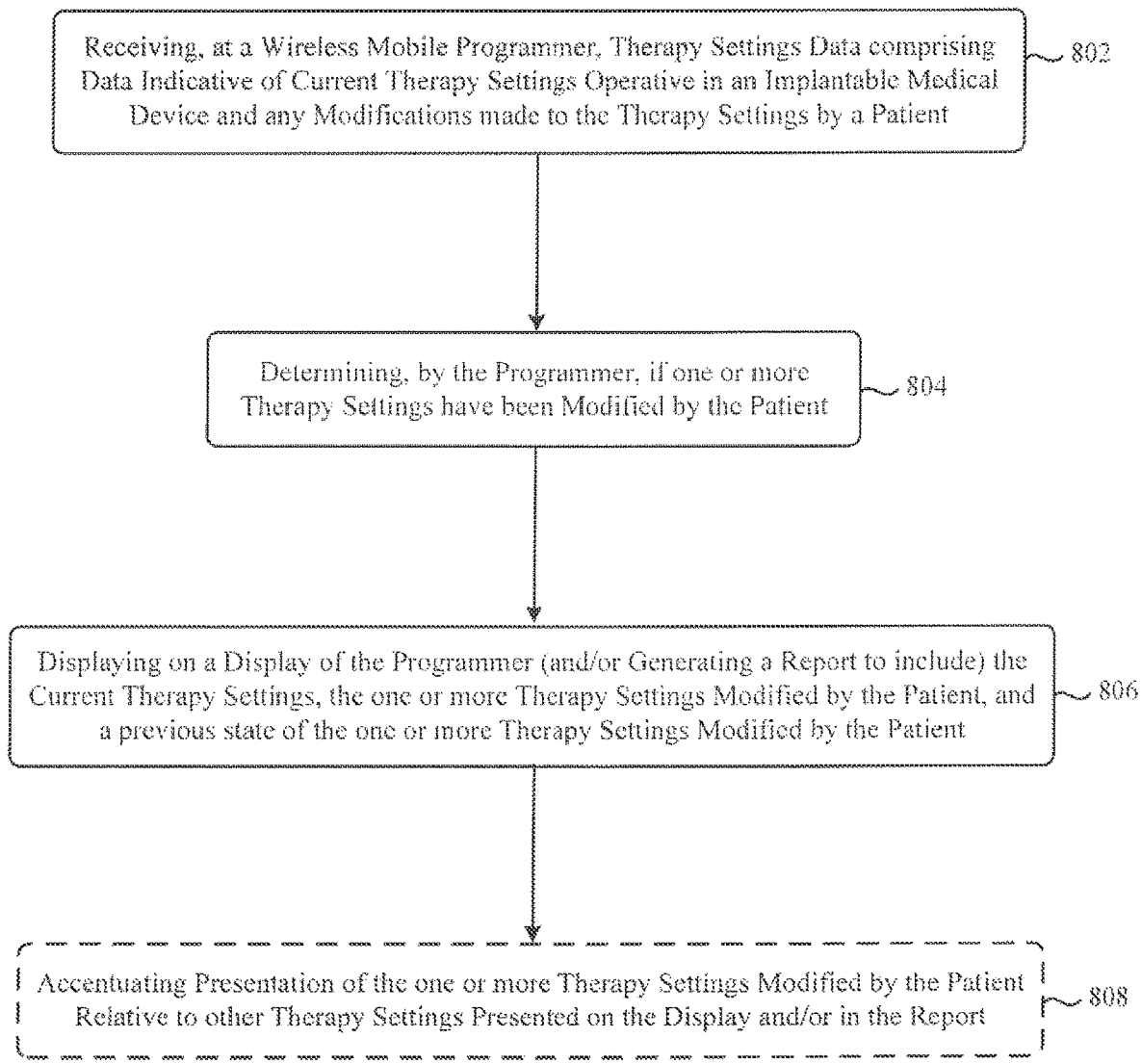
FIGS. 8 and 9 illustrate methods for presenting patient modified therapy parameters in a conspicuous manner on a programmer communicatively coupled to the implantable medical device in accordance with various embodiments.
Figure 9:
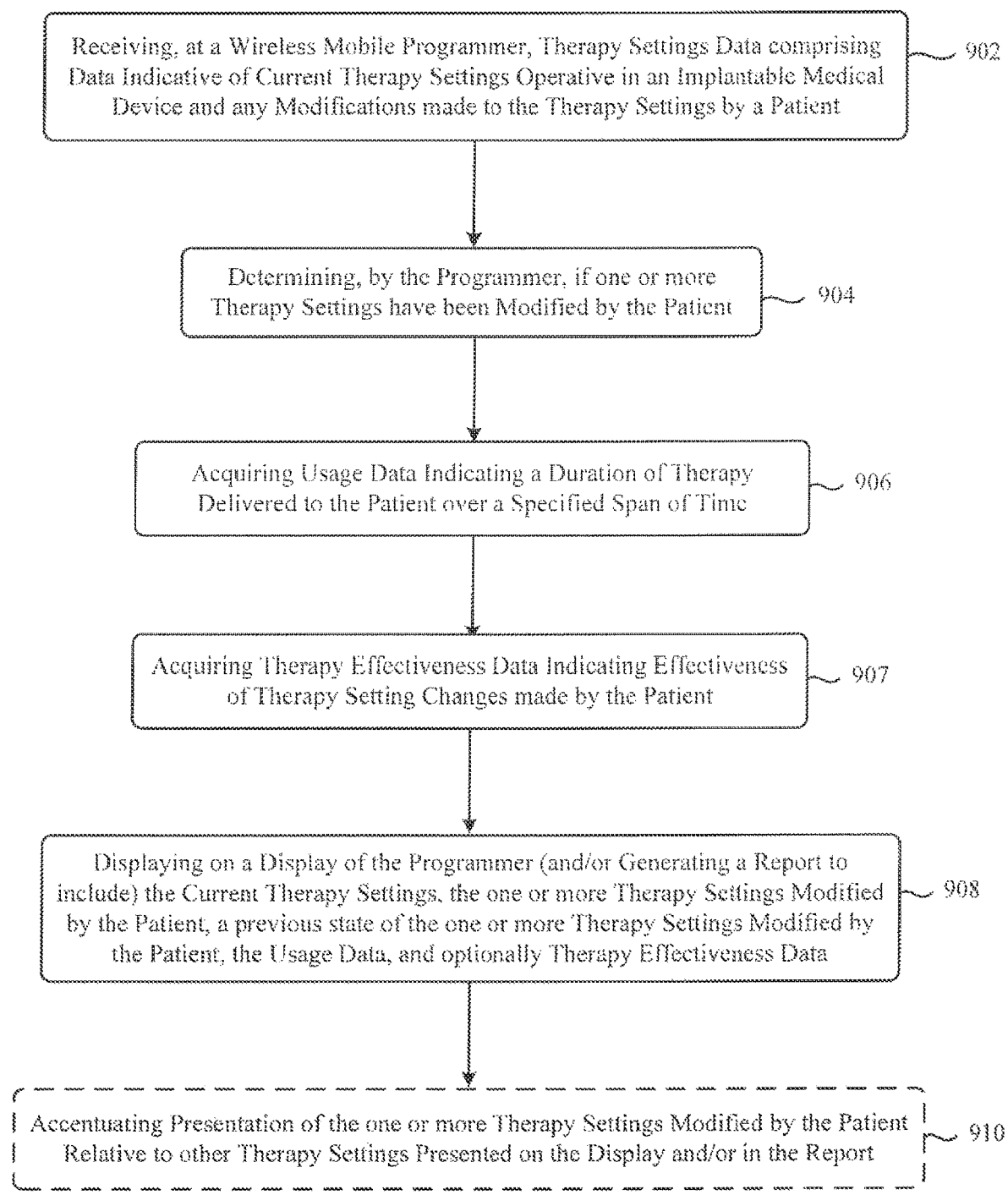

FIGS. 8 and 9 illustrate methods for presenting patient modified therapy parameters in a conspicuous manner on a programmer communicatively coupled to the IMD in accordance with various embodiments. In some embodiments, the programmer is configured as a wireless mobile programmer of the type described previously herein. In other embodiments, the programmer may be a stationary programmer, such as one enabled by a desktop PC or other relatively stationary processing device. For purposes of illustration and not of limitation, the embodiment illustrated in FIG. 8 will be described in the context of a wireless mobile programmer.

The methodology shown in FIG. 8 involves receiving 802, at a wireless mobile programmer, therapy settings data comprising data indicative of current therapy settings operative in an IMD and any modifications made to the therapy settings by a patient and optionally by the IMD. The methodology illustrated in FIG. 8 also involves determining 804, by the programmer, if one or more therapy settings have been modified by the patient and optionally by the IMD. The method shown in FIG. 8 further involves displaying 806 on a display of the programmer (and/or generating a report to include) the current therapy settings, the one or more therapy settings modified by the patient and optionally by the IMD, and a previous state of the one or more therapy settings modified by the patient and optionally by the IMD. In some embodiments, the method shown in FIG. 8 may involve accentuating 808 presentation of the one or more therapy settings modified by the patient relative to other therapy settings presented on the display of the programmer and/or in a report. In addition to displaying on the programmer and/or generating a report, the current therapy settings and modification by the patient and optionally by the IMD can also be saved (e.g., in a report) for output or download.

The methodology illustrated in FIG. 9 involves receiving 902, at a wireless mobile programmer, therapy settings data comprising data indicative of current therapy settings operative in an IMD and any modifications made to the therapy settings by a patient and optionally by the IMD. The method shown in FIG. 9 also involves determining 904, by the programmer, if one or more therapy settings have been modified by the patient and optionally by the IMD, and acquiring 906 usage data indicating a duration of therapy delivered to the patient over a specified span of time. The usage data can be associated with each set of therapy settings utilized over the specified span of time, so as to reveal which set of therapy settings were used most and the usage results associated with each.

In some embodiments, the method involves determining 907 the effectiveness of therapy setting changes made by the patient and optionally by the IMD, such as by analyzing various data acquired by the IMD and/or the patient remote or other external devices and sensors (e.g., oxygen desaturation index (ODI), apnea-hypopnea index (AHI), snoring index (SI), maximum nocturnal sound intensity, patient motion, etc.). For example, one or more of ODI, snoring, oximetry, nocturnal motion, and respiratory noise can be collected by the patient remote or other external device and used to determine a useful AHI estimate. Changes in the AHI estimate can be monitored to assess effectiveness of therapy setting changes made by the patient or automatically.

The processes of blocks 902-907 thus involve determining if one or more therapy settings have been modified by the patient and optionally by the IMD, acquiring usage data indicating a duration of therapy delivered to the patient over a specified span of time or times, and the effectiveness or lack of effectiveness of any such therapy changes. Usage data may be acquired from the patient remote, the patient remote via a web-based patient management system, another external device or system, or from the IMD. In some embodiments, the data acquired by the programmer and/or patient remote or other external device, including usage data, can be downloaded (as data or in report form) via a web-portal based on data collected and sent to this portal from the patient remote or the IMD. This content can be identical to what is made available on the display of the programmer.

In some embodiments, the patient remote or other external device in communication with the IMD can be configured to collect various objective therapy metric data, such as that listed above, and implement an auto-titration algorithm that computes recommended therapy setting changes for the IMD. The patient remote or other external device can cooperate with the IMD to modify the therapy settings using the recommended changes. In some embodiments, collection of objective therapy metric data, computing recommended therapy setting changes, and effecting such changes in the IMD occur automatically, without intervention by the patient. In this regard, one or both of the patient remote/external device and the IMD can be configured to automatically make therapy setting changes to the IMD. The patient remote/external device can subsequently collect the various objective therapy metric data and assess the efficacy of the recommended therapy setting changes. The results of this efficacy assessment may be communicated to an external system and/or programmer, and the auto-titration process can continue to fine-tune the therapy setting changes.

Figure 22:
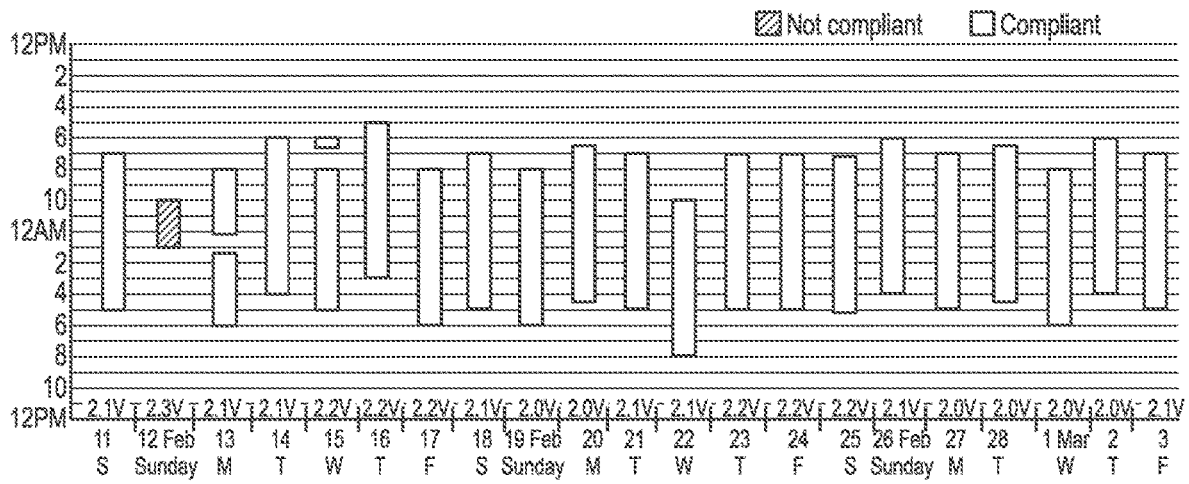
FIG. 22 is a representative display of information presented in a sleep log format that communicates the time and duration of therapy for each day.

The methodology illustrated in FIG. 9 further involves displaying 908 on a display of the programmer (and/or generating a report to include) the current therapy settings, the one or more therapy settings modified by the patient and optionally by the IMD, a previous state of the one or more therapy settings modified by the patient and optionally by the IMD, the usage data, and optionally therapy effectiveness data. For example, the method may involve calculating times of delivered therapy per day using the usage data, and displaying or reporting the usage data may involve displaying and/or reporting the therapy on time for each day (or a graphical representation thereof) over a predetermined duration of time, such as at least a period of one week. Therapy effectiveness data can be displayed or reported to indicate whether or not, and to what extent, patient and optionally IMD changes to therapy settings has improved the patient's condition. An illustrative report showing this information is provided in FIG. 22. The information shown in FIG. 22 is of a sleep log type that communicates the time and duration of therapy for each day and therapy amplitude, and also includes compliance and non-compliance information.

In some embodiments, the methodology shown in FIG. 9 may involve accentuating 910 presentation of the one or more therapy settings modified by the patient relative to other therapy settings presented on the display and/or in a report. In other embodiments, the therapy settings associated with the highest therapy compliance and/or best therapy efficacy can be identified, and can be accentuated on the display and/or in a report. In addition to displaying on the programmer, the therapy usage data can also be saved (e.g., in a report) for output or download. Associating and displaying the various therapy settings with usage and effectiveness data allows the clinician to modify therapy settings to maximize usage and effectiveness. For example, displaying usage data, associated therapy settings, and therapy efficacy data together (e.g., at the same location on the display) can facilitate clinician evaluation of and modifications to the therapy settings to enhance usage and effectiveness.

The methods disclosed herein may involve reporting information concerning patient and optionally by the IMD modification of therapy settings in a variety of different ways. For example, reporting patient modification of one or more therapy settings may involve dispatching a message or a report indicating patient modification of the one or more therapy settings to a remote device. Some embodiments may involve generating control signals by a patient remote to effect modification of one or more therapy settings of the IMD, and presenting information on a display of the patient remote or a device communicatively coupled to the patient remote notifying the patient of the modification to the one or more therapy settings. For example, the patient remote or device communicatively coupled to the patient remote (e.g., cloud- or web-mediated remote programming) may notify the patient to review parameter values based on the therapy parameter modifications made by the patient (e.g., patient changes to amplitude, system flag amplitude limit parameters).

Other embodiments may involve generating, at a patient remote configured to communicatively couple to the IMD, a first control signal requesting modification of one or more therapy settings of the IMD, performing one or both of prompting the patient to confirm patient intent to modify the one or more therapy settings and recommending an alternative modification to the one or more therapy setting, and generating, at the patient remote, a second control signal to effect the requested or alternative modification to the one or more therapy settings. In some embodiments, prompting is implemented by the patient remote, while in other embodiments, prompting is implemented by a device communicatively coupled to the patient remote (e.g., a smartphone running an appropriate app).

Figures 10, 11:
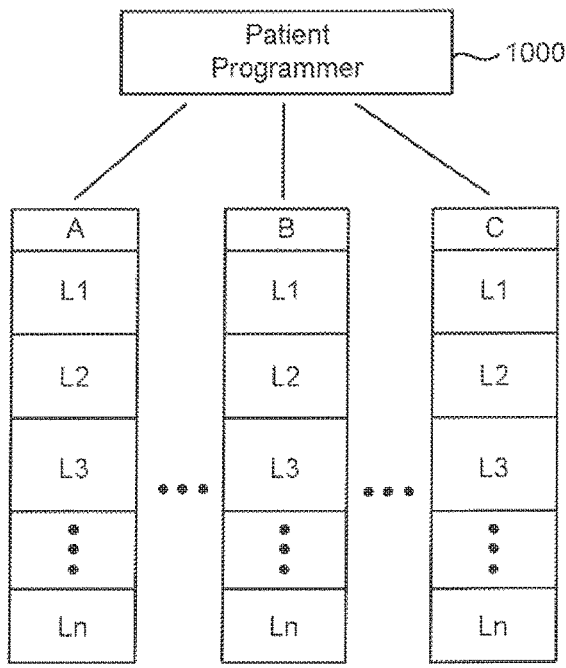
FIG. 10 shows a representative patient remote configured to facilitate patient adjustment of up to three different therapy parameters, shown as parameters A, B, and C in accordance with various embodiments.
FIG. 11 is a chart of representative information about each of the three parameters A, B, and C shown in FIG. 10 that can be monitored, stored, and subsequently evaluated by a clinician in accordance with various embodiments.

According to some embodiments, various types of information about therapy setting changes made by the patient can be recorded by one or both of the IMD and the patient remote, and this information can be transmitted to the clinician for evaluation. With reference to FIGS. 10 and 11, a representative patient remote 1000 is configured to facilitate patient adjustment of up to three different therapy parameters, shown as parameters A, B, and C. Parameter A may represent stimulation signal strength or amplitude, parameter B may represent stimulation signal rate, and parameter C may represent stimulation signal pulse width. Reference is made to FIG. 12 which shows each of these representative parameters (amplitude, rate, pulse width) superimposed on an illustrative stimulation waveform. According to various embodiments, stimulation amplitude is represented in terms of volts, and is considered the primary adjustment parameter made available to the patient. Pulse width, which is the stimulation waveform duration, is represented in terms of microseconds, and is considered a secondary adjustment parameter which affects the gross strength the stimulation energy. Rate is represented in terms of pulses per second or Hertz, and is considered a secondary adjustment parameter which controls smoothness of the stimulation sensation. It is noted that adequate airway patency during inspiration can be achieved for most patients by adjusting the stimulation amplitude only. In some embodiments, the patient is permitted change only the stimulation amplitude setting. In other embodiments, the patient may be permitted to change other parameters in addition to stimulation amplitude, such as pulse width and rate, for example.

It is understood that other stimulation signal parameters are contemplated, and that the number and types of parameters alterable by the patient as described herein are provided for illustrative purposes and not of limitation. In the representative embodiment shown in FIG. 13, for example, a patient remote 1300 includes control buttons for adjusting a number of different therapy parameters. In this illustrative example, the patient remote 1300 includes an amplitude increase button 510, and amplitude decrease button 512, a rate increase button 1302, a rate decrease button 1304, a pulse width shorten button 1306, and a pulse with lengthen button 1308. A control button 1310 is provided to allow selection between a number of different stimulation signal morphologies, each of which has a different impact on the therapy delivered to the patient. For example, a first stimulation waveform version may be characterized by a train of fixed duration pulses, while a second stimulation waveform version may be characterized by a train of fixed duration pulses interspersed with high-frequency short duration pulses.

Each of therapy parameters A, B, C shown in FIG. 10 has a number of different parameter settings or levels, L1-Ln, which can be individually selected by the patient. It is noted that the total number of parameter settings or levels for the different therapy parameters can be the same or differ. As was discussed previously, the number and/or range of possible patient adjustable parameter settings are based at least in part on the parameter range established by the clinician. In some embodiments, the clinician defines the number of different therapy setting levels as well as therapy setting increments between each level. In other embodiments, an algorithm can automatically determine the number of selectable therapy setting levels as well as the therapy setting increments between each level. For purposes of illustration, it can be assumed that parameter A represents stimulation amplitude, and that the stimulation strength controls 510 and 512 shown in FIG. 5A can be used by the patient to increase and decrease the strength of stimulation delivered by the IMD. The IMD may be programmed to default to a middle-strength amplitude, such as an amplitude corresponding to level L3. Pressing the stimulation increase button 510 causes the stimulation amplitude to increase in a step-wise fashion from an amplitude specified for level L3 to higher stimulation amplitude levels, such as L4, L5 or L6, for example. Pressing the stimulation decrease button 512 causes the stimulation amplitude to decrease in a step-wife fashion from an amplitude specified for level L3 to lower stimulation amplitude levels, such as L2 or L1, for example. The patient may adjust other parameters, such as parameters B and C, in a similar manner.

According to some embodiments, the amount or percentage of time each therapy parameter is active at each therapy level can be monitored and stored for subsequent assessment by the clinician. Reference is made to FIG. 11 which is a chart of representative information about each of the three parameters A, B, and C that can be monitored, stored, and subsequently evaluated by a clinician in accordance with various embodiments. It is understood that the therapy parameter information shown in FIG. 11 is provided for illustrative, non-limiting purposes. The information recorded in FIG. 11 includes the percentage or amount of time the IMD delivered therapy at each of the specified parameter levels are settings, L1-Ln. A trend or histogram of these data can be generated and stored, allowing the clinician to evaluate changes that occur to the therapy parameter settings over time, such as in a calendar-type manner. Storing a history of therapy parameter changes over a period of time allows the clinician to apply various trending algorithms to the data. For example, the clinician may view the trend data to determine whether the therapy setting changes made by the patient fit a typical profile (a pattern of progressive increases or decreases) or whether such changes are relatively random. If random, this may suggest that the patient requires training or other form of intervention.

Other useful information may be associated with each of the different therapy parameters and parameter settings, such as various diagnostic indices. For example, an apnea-hypopnea index (AHI) and/or an oxygen desaturation index (ODI) can be associated with each setting or level (e.g., L1-Ln) of each therapy parameter (e.g., A-C). Other data, such as snorting (SI) data, nocturnal sound intensity, and nocturnal motion data, can be collected and associated with each setting or level of each therapy parameter. Associating AHI and/or ODI or other diagnostic indices can provide additional information about the efficacy of a patient's therapy parameter adjustments. Therapy parameter and usage data may be associated with objective therapy metrics, such as snoring, respiratory sonic data (e.g., sonic spectrographs), nocturnal motion, oximetry, and ODI/AHI, or subjective therapy metrics such as a sleep questionnaire, for example. For example, ODI may be collected on the patient remote, an AHI may be collected by the IMD (or by the patient remote using the microphone situated in proximity to the patient during sleep), and quality of life (QOL) questionnaires may be implemented via a web portal, a phone app, or on the patient remote itself. In some implementations, one or more flags can be used to indicate when a particular diagnostic index has exceeded a predetermined threshold. The flag can be set by the IMD, the patient remote 1000, the programmer, or a combination of these devices.

Other useful information may also be associated with each of the different therapy parameters and parameters, such as therapy usage and therapy effectiveness. For example, the number of hours used per night can be associated with each setting or level.

Figure 14:
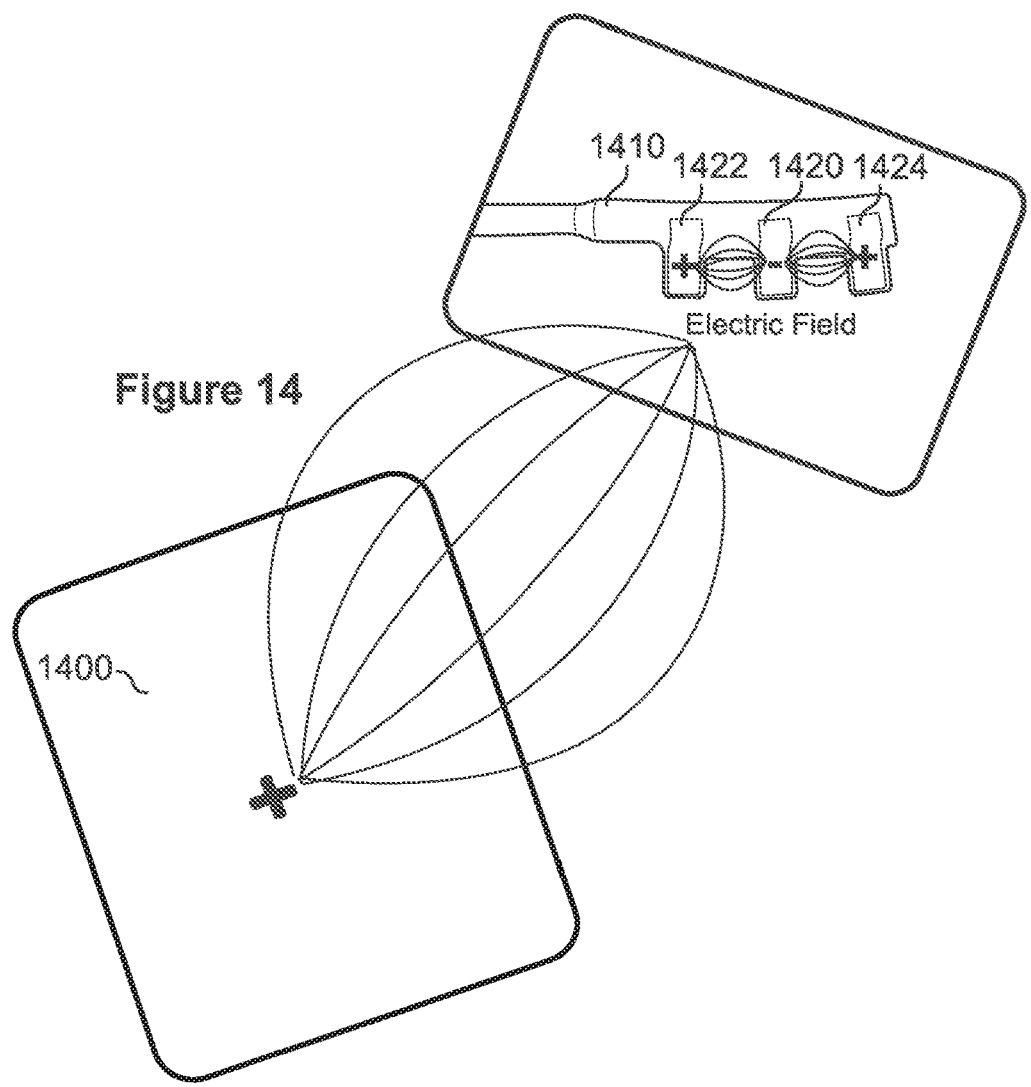
FIG. 14 shows a representative neurostimulation apparatus which includes an implantable neurostimulator electrically coupled to a stimulation lead in accordance with various embodiments.
Figure 15:
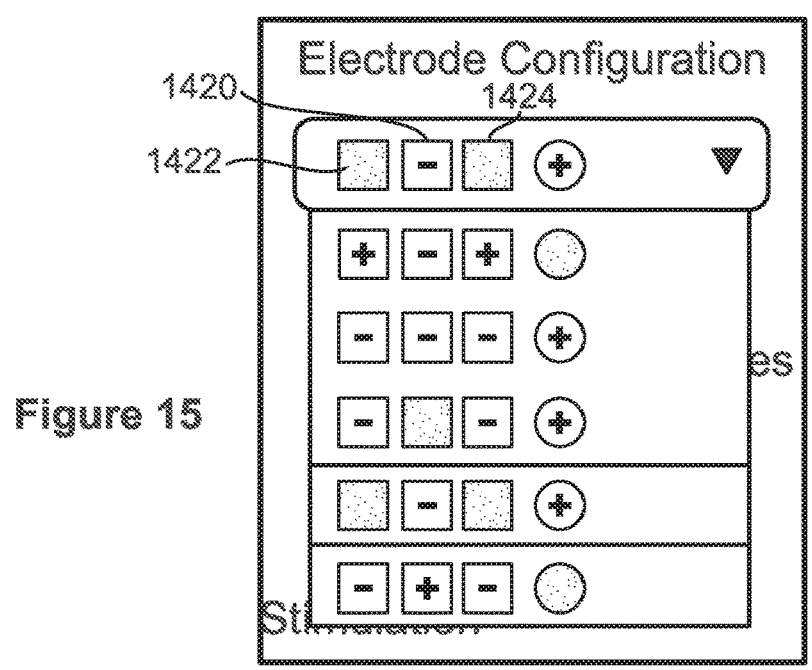
FIG. 15 shows the various electrode configurations or vectors for the stimulation lead shown in FIG. 14 that can be selected in accordance with various embodiments.

FIGS. 14 and 15 show an embodiment of a neurostimulation apparatus in accordance with various embodiments. The neurostimulation apparatus shown in FIG. 14 includes an implantable neurostimulator 1400 electrically coupled to a stimulation lead 1410 having a stimulation electrode 1405. The stimulation electrode 1405, which may be configured as a cuff electrode, includes a number of electrodes, three of which are shown as electrodes 1420, 1422, and 1424 in the embodiment shown in FIG. 14. The case or housing of the neurostimulator 1400 can serve as a far-field electrode in some configurations, but is typically electrically inactive in a standard electrode configuration. FIG. 15 shows the various electrode configurations or vectors that can be selected by the clinician and, in some embodiments, by the patient via the patient remote (e.g., via the waveform version button 310 shown in FIG. 13 or a separate electrode configuration button). In accordance with embodiments that allow patient selection of stimulation electrode configuration, different combinations of electrodes can be activated and deactivated by activation of an appropriate control button (e.g., waveform version button 1310) on the patient remote.

Figure 16:
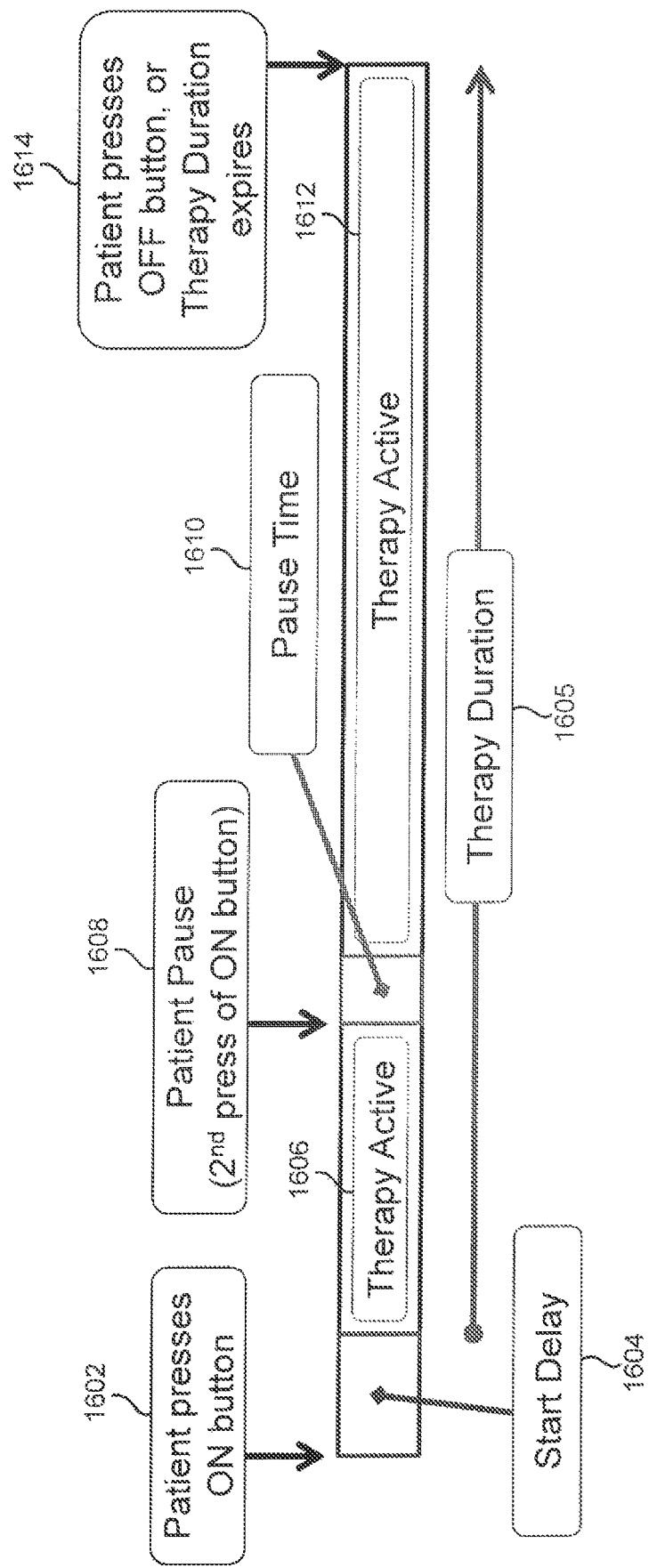
FIG. 16 illustrates various activities associated with delivering neurostimulation therapy for treating obstructive sleep apnea in accordance with various embodiments.

FIG. 16 illustrates various activities associated with delivering neurostimulation therapy for treating obstructive sleep apnea in accordance with various embodiments. Using the patient remote, the patient activates therapy 1602 prior to falling asleep, such as by pressing the therapy ON button 502 shown in FIG. 6. Activation of the therapy ON button 502 initiates a start delay 1604. The patient may verify that therapy is active by looking for illumination of the therapy ON indicator 522 provided on the rear surface of the patient remote, as shown in FIG. 5B. The start delay 1604 (also referred to herein as therapy delay) represents a predetermined delay period (e.g., 30 minutes) during which stimulation therapy is withheld or prevented, allowing the patient to fall asleep prior to actual delivery of neurostimulation therapy, thus avoiding any discomfort associated with neurostimulation while not yet asleep.

After expiration of the start delay 1604, neurostimulation therapy automatically turns on. The patient may pause 1608 therapy delivery anytime during the night by pressing the therapy ON button 502 shown in FIG. 6, such as when awaking to use the bathroom. Therapy delivery is paused for a predetermined duration of time, such as 15 minutes, to allow the patient to fall back asleep, after which therapy delivery automatically turns on. The total amount of pause time 1610 throughout the night is recorded, as is the total duration of the one or more therapy active period(s) 1612. Stimulation therapy is terminated by one of two events; either the patient presses the therapy OFF button 506 shown in FIG. 5A or by expiration of the therapy duration timer, which is typically set to a total duration of eight hours. The total duration of therapy delivered to the patient, which is an accumulation of all therapy active periods 1606, 1612 during the evening, is calculated and stored. It is noted that the total duration of actual therapy delivery is typically less than the total amount of time between initiation 1602 and termination 1614 of therapy by the patient's use of the patient remote due to the start delay and one or more pause periods.

FIG. 17 is a screen 1700 of an application interface provided on a display of a programmer showing various therapy parameters of an IMD, such as a neurostimulator, that can be adjusted by a clinician in accordance with various embodiments. In some embodiments, some or all of the therapy parameters are established by a clinician, and are input by the clinician as initial therapy settings. In other embodiments, some or all of the initial therapy settings are predetermined as default settings, which may subsequently be modified by the clinician. Establishing the initial therapy settings may involve using predetermined therapy settings based on patient population data, clinical trial research, and/or diagnostic information determined for a particular patient.

The programmable parameters shown in FIG. 17 include an amplitude parameter 1702, which is shown to have a value of 2.0 V in this illustrative example. A patient control amplitude range 1704 is defined to include a lower limit and an upper limit, shown as 1.8 V and 2.8 V respectively in FIG. 17. In one embodiment, the lower and upper limits of the patient control amplitude range 1704 are established by the clinician. In other embodiments, a functional threshold (FT) 1706 can be defined by the clinician, which is used to automatically compute the lower and upper amplitude range limits 1704. For example, a processor of the programmer can compute the patient control amplitude range 1704 using the formula FT+x volts (e.g., 1.0 V) divided by n steps (e.g., 11 steps). In this illustrative example, the computed result is given by 2.0 V+1.0 V÷3 V/11=2.072. The lower and upper amplitude range limits 1704 is computed as the programmed amplitude value (e.g., 2.0 V)−/+the computed result (e.g., 2.07), which, when rounded, results in a range of 1.8 V to 2.8 V, with 11 discrete voltage steps in between these two limits. Accordingly, the patient remote can be used by the patient to adjust the clinician programmed amplitude within a range computed as described above or established by the clinician, with 11 discrete voltage steps in between each adjustment within the established amplitude range.

Other therapy parameters that can be established by the clinician include the electrode configuration 1710 which, in accordance with some embodiments, can be subsequently modified by the patient using the patient remote as discussed previously. Various therapy timing parameters can be established by the clinician, including start delay 1720 (e.g., 30 minutes), pause time 1722 (e.g., 15 minutes), and therapy duration 1724 (e.g., 8 hours). Various parameters associated with the stimulation waveform can be selected by the clinician, including pulse width 1730 (e.g., 90 μs), frequency 1732 (e.g., 33 Hz), and maximum stimulation time (e.g., 4 seconds). Other programmable therapy parameters include exhalation 1740 (e.g., −4/−1), inhalation 1742 (e.g., 0/+1), OFF period 1744 (e.g., 38/13), and signaling version 1750. The exhalation parameters determine the detection of the start of exhalation phase of the respiratory cycle, whereas inhalation parameters determine the detection of the start of inhalation phase of the respiratory cycle. The stimulation delivery is prohibited during the OFF period based on its programming.

FIG. 18 is a screen 1800 of an application interface showing various therapy settings on a display of a programmer in accordance with various embodiments. The parameter screen 1800 includes patient identification section 1802, and actions section 1804, a report section 1806, a patient details section 1808, a patient therapy status section 1810, a stimulation section 1830, and a sensing section 1860. The patient identification section 1802 allows various information identifying the patient be input and modified. The actions section 1804 allows for clinician actuation of various features, such as recording thresholds, adjusting stimulation parameters 1805, and adjusting sensing parameters. Various reports can be generated by actuation of one or more buttons in the reports section 1806. Various patient details can be input, reviewed, and modified in the patient details section 1808.

The screen 1800 includes a number of parameters that impact patient therapy status 1810, stimulation parameters 1830, and sensing parameters 1860. The patient therapy section 1810 includes information concerning the stimulation amplitude 1812 and any changes made thereto by the patient, battery status 1818, and therapy usage 1820. A device therapy section (not shown) can be included for displaying information concerning various automated device-initiated changes made to therapy settings. Alternatively, the patient therapy section 1810 can display patient-initiated therapy changes in a manner that differs from device-initiated therapy changes (e.g., different colors, different, fonts, indicia differentiating patient-from device-initiated therapy changes). In the embodiment shown in FIG. 18, a patient change to the stimulation amplitude 1812 is reflected by presentation of the current state of the amplitude selected by the patient (2.2 V) followed by presentation of the previous state of the amplitude (2.3 V). An indicator 1816, such as a "patient made change" indicator, is presented on the screen 1800 next to the amplitude change information so as to alert the clinician to the change in stimulation amplitude made by the patient. A different indicator 1817 can be presented to indicate no change was made by the patient. In general, the change in stimulation amplitude or other therapy parameter modified by the patient is accentuated in some way so as to call attention to the change when the clinician accesses this information on the screen 1800. This change information can be accentuated in a number of ways, such as by a change in font, bolding, underlining, coloring, and/or the addition of graphical or textual indicia (e.g., message 1816). An audio message or sound can also be broadcast to draw clinician attention to a programming change made by the patient.

The stimulation section 1830 includes changes made by the clinician to various stimulations therapy settings during a patient visit. In the illustrative example shown in FIG. 18, the encircled region indicates the stimulation parameters that have been changed by the clinician during the current programming session, which include the stimulation amplitude 1832 (changed from 2.3 V to 2.0 V). The patient control range 1834 is also accentuated to show changes made thereto. As was previously discussed, the patient control range 1834 can be established manually or via an algorithm executed by a processor of the programmer. Other stimulation parameters include start delay 1835, pause time 1836, and therapy duration 1838.

Figure 19:
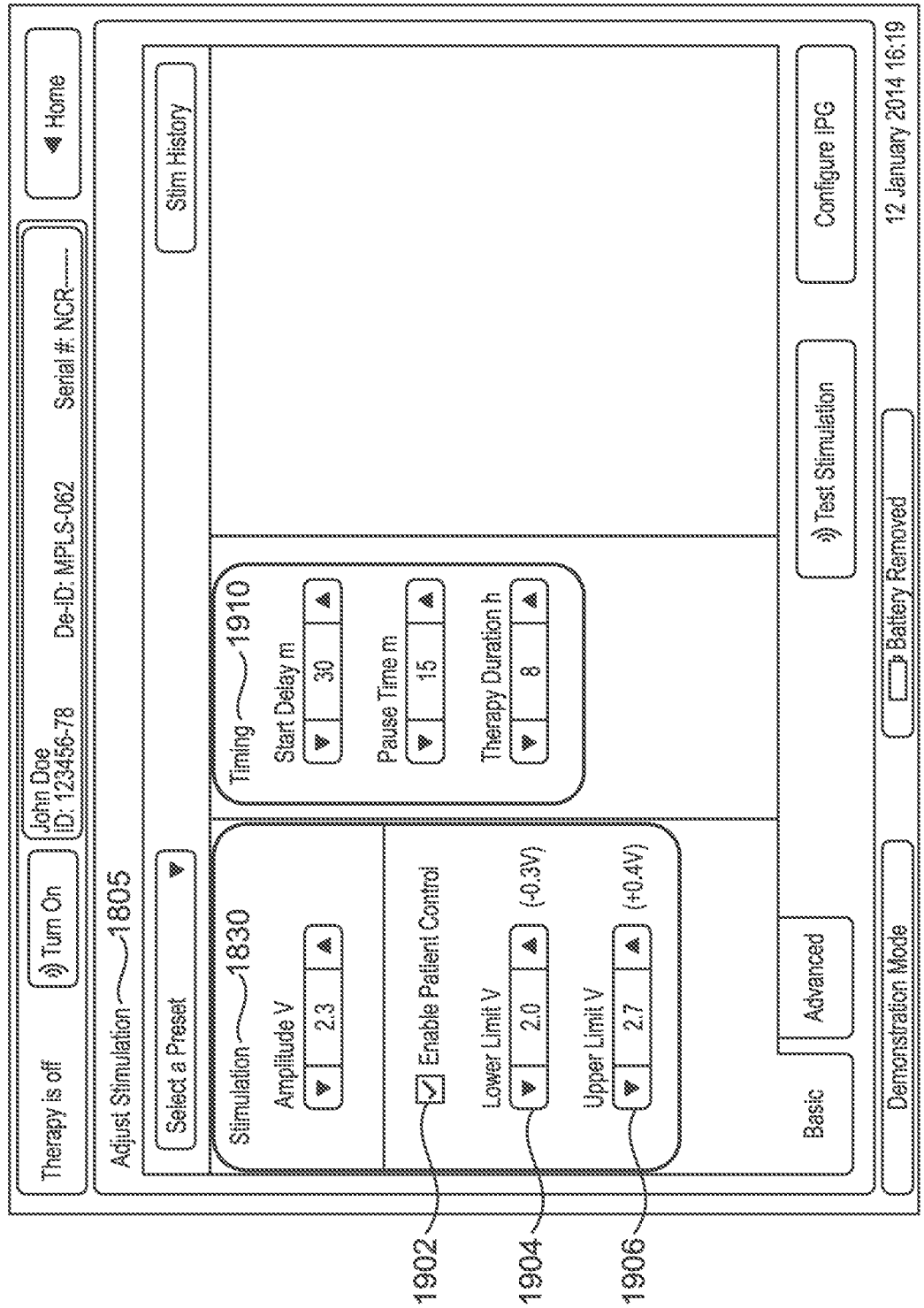
FIG. 19 shows various settings that can be adjusted by a clinician, including stimulation amplitude and limits that define a patient-controllable stimulation amplitude range in accordance with various embodiments.

FIG. 19 shows various settings that can be adjusted from the adjust stimulation section 1805 (see also FIG. 18). The adjust stimulation section 1805 allows the clinician to adjust the stimulation amplitude 1830, various timing parameters 1910, and enable or disable control 1902 of the stimulation amplitude by the patient remote. When control 1902 of stimulation amplitude is enabled, the lower limit 1904 and upper limit 1906 can be adjusted manually or algorithmically as previously discussed. In general, and for established patients, the therapeutic amplitude control limits 1904 and 1906 are generally set to steps below and above the patient's titrated stimulation amplitude. Any change in either the upper or lower limits 1904 in 1906 from a previous setting is accentuated for each of the lower and upper limits 1904 and 1906 (e.g., a reduction of 0.3 V in the lower limit and an increase of 0.4 V in the upper limit is indicated by the gray colored text in parentheses).

Figure 20:
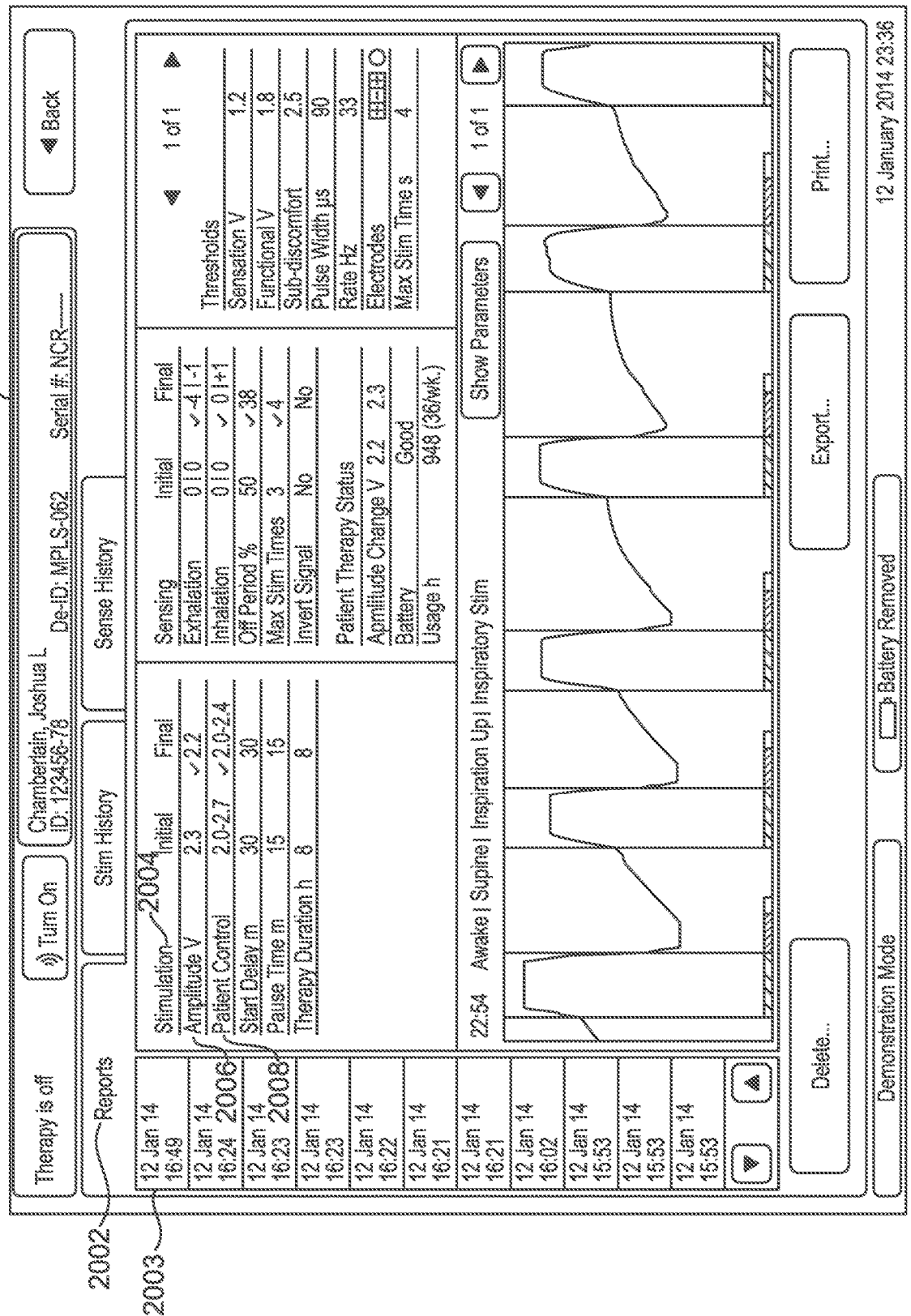
FIG. 20 is a screen of an application interface showing information concerning a multiplicity of programming sessions conducted over the course of a single day in accordance with various embodiments.
Figure 21:
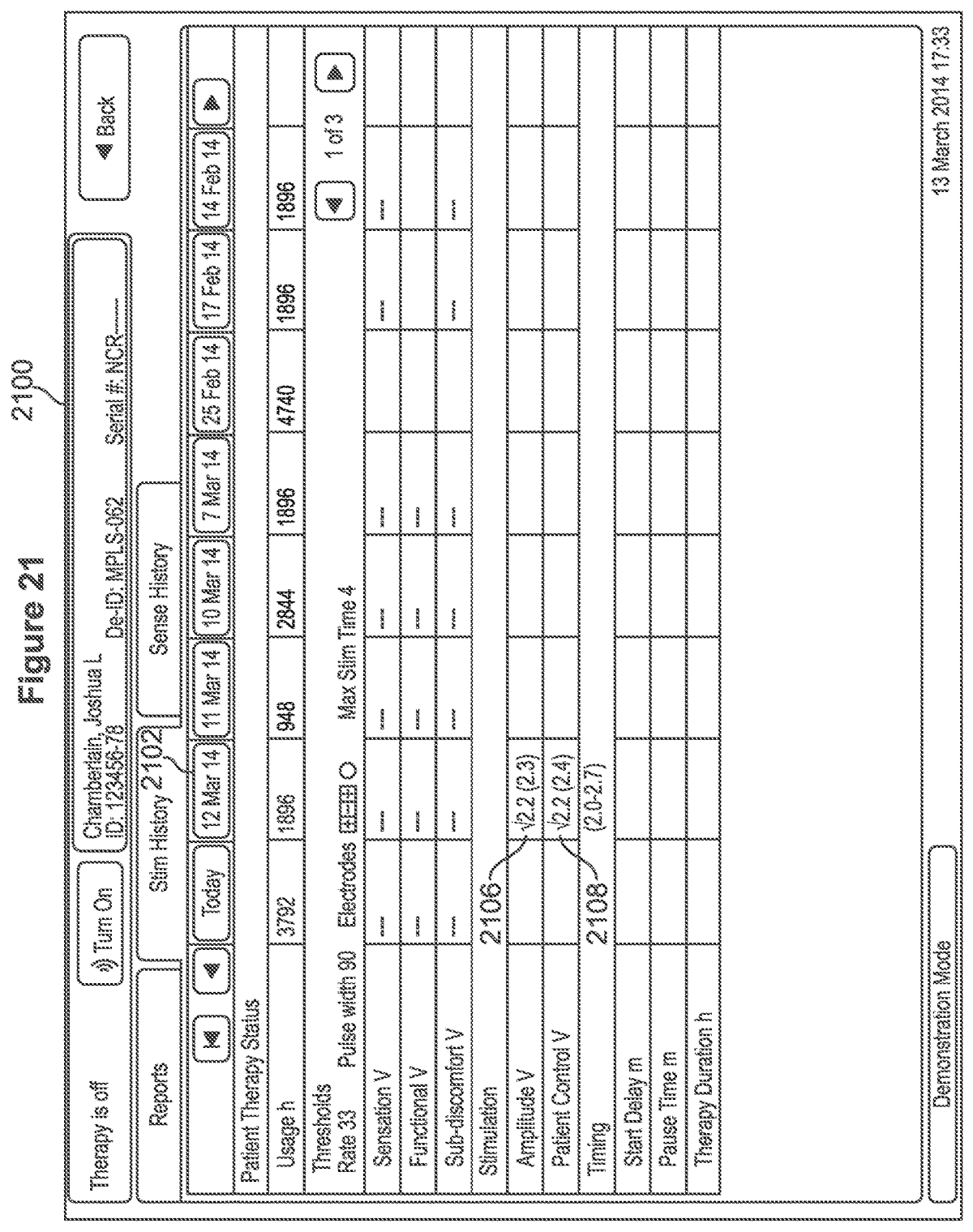

FIGS. 20 and 21 illustrates therapy parameter information that can be generated by a programmer including the initial and final states of therapy setting that have been modified during a multiplicity of time-separated programming sessions in accordance with various embodiments. In some embodiments, programming of an IMD for a particular patient occurs during each of a multiplicity of individual programming sessions that extend over a given period of time, such as during an evening. During each individual programming session, one or more therapy parameters can be modified by the clinician. Although it may be possible to generate a report concerning the initial and final states of therapy settings for each individual programming session, therapy setting changes that occur across several time-separated programming session are typically not accounted for nor easily determinable by the clinician. As a result, a clinician is typically required to evaluate each report from each individual programming session, and manually determine which, if any, therapy settings have changed from one session to another so that the initial and final states of all modified therapy settings over the course of the entire programming session can be determined.

Embodiments of the present disclosure are directed to a programmer configured to generate a summary report based on programming that occurred during a multiplicity of programming sessions. Various embodiments are directed to a method of programming an IMD, such as a neurostimulator, using a wireless mobile programmer or other type of programmer during each of a plurality of time-separated programming sessions comprising at least a first programming session and a last programming session. The method involves establishing initial therapy settings of the IMD during the first programming session, modifying one or more of the therapy settings during one or more programming session subsequent to the first programming session, and generating a summary based on programming that occurred during the programming sessions. According to some embodiments, the summary comprises a current state of any therapy setting that remained unchanged between the first and last programming sessions, a final state of any therapy setting that was modified between the first and last programming sessions, and initial state of any therapy setting that was modified between the first and last programming sessions. The method further involves presenting the summary on a display of the programmer or other output device or media.

According to some embodiments, generating the summary involves generating a session summary for each programming session. The session summary can include an indication of final therapy settings for each programming session that were unchanged during the programming session, and an indication of an initial state of any final therapy setting that was modified during each programming session. The method further involves presenting the session summaries on the display or other output device or media. In some embodiments, presenting the summary involves accentuating presentation of the final state and/or the initial state of any therapy setting that was modified between the first and last programming sessions. Some embodiments involve determining an aggregate duration of the multiplicity of time-separated programming sessions, and presenting the aggregate duration on the display or other output device or media. For example, the method may involve determining a duration of each of the plurality of time-separated programming sessions, determining an aggregate duration of the plurality of time-separated programming sessions, and presenting the duration and aggregate duration on the display or other output device or media.

FIG. 20 is a screen 2000 of an application interface showing information concerning a multiplicity of programming sessions conducted over the course of a single day (or night) in accordance with various embodiments. The particulars of each individual programming session can be reviewed by the clinician clicking on a given programming session under the Reports tab 2002. In this illustrative embodiment, the programming session reports under the Report tab 2002 contain information about each of a multiplicity of time-separated programming sessions of a patient's sleep study conducted over the course of an evening. Modifications to various therapy settings that occurred during the programming session highlighted as session 2003 are summarized in the stimulation section 2004. During the programming session 2003, the stimulation amplitude was changed by the clinician from 2.3 V to 2.2 V, and the patient control range was changed from 2.0-2.7 V to 2.0-2.4 V. Similar changes may have occurred during each of the other programming sessions shown under the Reports tab 2002.

FIG. 21 is a screen 2100 of an application interface showing a summary report that provides a clear indication of the initial and final states of any therapy setting that was modified between the first and last programming sessions of a multi-programming session sleep study in accordance with various embodiments. The therapy setting changes made over the course of multiple programming sessions shown in FIG. 20 are summarized under the tab 2102 entitled 12 Mar 14. It can be seen under tab 2102 (for 12 Mar 14) that the amplitude was changed from an initial state of 2.3 V to a final state of 2.2 V sometime during the multiple programming session event. It can also be seen that that patient control range was changed from an initial state of 2.0-2.7 V to a final state of 2.2-2.4V sometime during the multiple programming session event. The changed state of these therapy parameters is accentuated by a check mark indicator in this illustrative example. It is noted that other data for other programming days/nights has been excluded for purposes of simplicity of explanation.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:
1. A method, comprising:
receiving, at a computing device, data indicative of therapy delivered by an implantable medical device configured to deliver neurostimulation therapy and any modifications made to the therapy via a patient remote;
acquiring stimulation setting data indicating modification of a therapy stimulation setting by the patient;
acquiring pause data indicating pauses in delivery of therapy; and
displaying, on a display, at least one of modification of a therapy stimulation setting by the patient and pause data;
wherein the neurostimulation therapy delivered by the implantable medical device comprises a therapy for treating sleep disordered breathing.

2. The method of claim 1, wherein the step of displaying is characterized by pause data not being displayed on the display.

3. The method of claim 1, further comprising:
acquiring usage data indicating daily patient therapy utilization; and
displaying, on the display, an indication of daily patient therapy utilization.

4. The method of claim 1, further comprising:
displaying, on the display, an indication of compliance or non-compliance with a therapy regimen for the patient.

5. The method of claim 4, further comprising:
determining if a duration of therapy delivered to the patient each day less a duration of the pauses indicates compliance or non-compliance with the therapy regimen.

6. The method of claim 4, further comprising:
determining if a duration of therapy delivered to the patient over a span of time indicates compliance or non-compliance with the therapy regimen.

7. The method of claim 1, wherein the modification of a therapy stimulation setting by the patient comprises at least one of an increase in stimulation strength and a decrease in stimulation strength.

8. The method of claim 7, wherein the patient remote allows the patient to increase the stimulation strength within a pre-set range, and decrease the stimulation strength within a pre-set range.

9. The method of claim 1, further comprising:
associating the usage data with a set of therapy settings utilized over a specified span of time.

10. The method of claim 9, further comprising:
displaying, on the display, which set of therapy settings were used most and the usage results associated with each set of therapy settings.

11. The method of claim 1, wherein the pauses in delivery of therapy are initiated by the patient via the patient remote.

12. The method of claim 1, wherein the pauses in delivery of therapy comprise a predetermined duration of time during which therapy is suspended.

13. The method of claim 1, further comprising:
displaying, on the display, a start delay period during which stimulation therapy is withheld.

14. The method of claim 13, wherein the start delay period is a predetermined time between receiving instructions at the patient remote to begin a therapy regimen and initiation of stimulation being delivered to the patient.

15. The method of claim 1, wherein the computing device comprises one of a clinician programmer and a smartphone.

16. The method of claim 1, wherein the step of displaying includes displaying both modification of a therapy stimulation setting by the patient and pause data on the display.

17. The method of claim 1, further comprising:
prior to the step of receiving:
implanting a neurostimulator of the implantable medical device in the patient; and
operating the implanted neurostimulator to apply electrical stimulation to the patient to treat sleep disordered breathing.

18. A computing device, comprising:
a display;
a processor comprising memory coupled to the display; and
an interface coupled to the processor and configured to receive data indicative of therapy delivered by an implantable medical device configured to deliver neurostimulation therapy and any modifications made to the therapy by a patient via a patient remote;
wherein the neurostimulation therapy delivered by the implantable medical device comprises a therapy for treating sleep disordered breathing;
wherein the processor is configured to:
acquire stimulation setting data indicating modification of a therapy stimulation setting by the patient,
acquire pause data indicating pauses in delivery of therapy, and
display, on the display, at least one of modification of a therapy stimulation setting by the patient and pause data.

19. The computing device of claim 18, wherein the processor is configured to not display pause data with the display of modification of a therapy stimulation setting by the patient.

20. The device of claim 19, wherein the processor is further configured to:
acquire usage data indicating daily patient therapy utilization; and
display, on the display, an indication of daily patient therapy utilization.

21. The device of claim 19, wherein the processor is further configured to:
display, on the display, an indication of compliance or non-compliance with a therapy regimen for the patient.

* * * * *